United States Patent
Gerner et al.

(10) Patent No.: US 6,258,845 B1
(45) Date of Patent: Jul. 10, 2001

(54) DFMO AND SULINDAC COMBINATION IN CANCER CHEMOPREVENTION

(75) Inventors: Eugene W Gerner, Tucson, AZ (US); Frank L. Meyskens, Jr., Irvine, CA (US)

(73) Assignees: The Regents of the University of California, Oakland, CA (US); Arizonia Board of Regents Behalf of the University of Arizonia, Tucson, AZ (US)

(*) Notice: Subject to any disclaimer, the term of this patent is extended or adjusted under 35 U.S.C. 154(b) by 0 days.

(21) Appl. No.: 09/277,688

(22) Filed: Mar. 26, 1999

Related U.S. Application Data

(60) Provisional application No. 60/079,850, filed on Mar. 28, 1998.

(51) Int. Cl.[7] .......................... A61K 31/195; A61K 31/19
(52) U.S. Cl. ............................................................. 514/544
(58) Field of Search .................................... 514/564, 569

(56) References Cited

U.S. PATENT DOCUMENTS

| | | | |
|---|---|---|---|
| 4,330,559 | 5/1982 | Bey et al. | 424/319 |
| 4,413,141 | 11/1983 | Bey et al. | 562/561 |
| 4,499,072 | 2/1985 | Sunkara et al. | 424/85 |
| 4,859,452 | 8/1989 | Ajani et al. | 424/10 |
| 4,925,835 | 5/1990 | Heston | 514/183 |
| 5,002,879 | 3/1991 | Bowlin et al. | 435/71.1 |
| 5,814,625 | 9/1998 | Larson et al. | 514/171 |
| 5,843,929 | 12/1998 | Larson et al. | 514/182 |

OTHER PUBLICATIONS

Alberts et al., "Do NSAIDs exert their colon cancer chemoprevention activities through the inhibition of mucosal prostaglandin synthetase?" *J. Cell. Biochem. Supp.*, (22):18–23, 1995.

Boyle et al., "Polyamine contents in rectal and buccal mucosae in human treated with oral difluoromethylornithine," *Cancer Epi Biomarkers Prev.*, 1:131–135, 1992.

Croghan et al., "Dose–related α–difluoromethylornithine ototoxicity," *Am. J. Clin. Oncol.*, (14):331–5, 1991.

Erdman et al., "Assessment of Mutations in Ki-ras and P53 in colon cancers from azoxymethane–and dimethylhydrazine–treated rats," *Mol. Carcin.*, (19):137–144, 1997.

Gann et al., "Low–dose aspirin and incidence of colorectal tumors in a randomized trial," *J. Natl. Cancer Inst.*, 85:1220–1224, 1993.

Gerner et al., "Gastrointestinal tissue polyamine contents of patients with Barrett's esophagus treated with a–difluoromethylornithine," *Cancer Epidemoil. Biomarkers Prev.*, 3:325–330, 1994.

Giardiello et al., "Ornithine decarboxylase and polyamines in familial adenomatous polyposis," *Cancer Res.*, (57):199–201, 1997.

Greenberg et al., "Reduced risk of large–bowel adenomas among aspirin users," *J. Natl. Cancer Inst.*, 85:912–916, 1993.

Hixson et al., "Sources of variability in measurements of ornithine decarboxylase activity and polyamine contents in colorectal mucosa," *Cancer Epidemoil. Biomarkers Prev.*, 3:317–323, 1994.

Hixson et al., "Ornithine decarboxylase and polyamines in colorectal nelplasia and mucosa," *Cancer Epidemiology Biomarkers Prev.*, 2:369–374, 1993.

Meyskens et al., "Dose de–escalation chemoprevention trial of α-difluoromethylornithine in patients with colon polyps," *J. Natl. Cancer Inst.*, 86(15):1122–1130, 1994.

Meyskens and Gerner, "Development of difluoromethylornithine as a chemoprevention agent for the management of colon cancer," *J. Cell. Biochem.*, 22:126–131, 1995.

Piazza et al., "Sulindac sulfone inhibits azoxymethane–induced colon carcinogenesis in rats without reducing prostaglandin levels," *Cancer Res.*, (57):2909–2915, 1997.

Piazza et al., "Antineoplastic drugs sulindac sulfide and sulfone inhibit cell growth by inducing apoptosis," *Cancer Res.*, (55):311 3116, 1995.

Piazza et al., "Apoptosis primarily accounts for the growth–inhibitory properties of sulindac metabolites and involves a mechanism that is independent of cyclooxygenase inhibition, cell cycle arrest, and p53 induction," *Cancer Res.*, (57):2452–2459, 1997.

Pollard and Luckert, "Prevention and treatment of primary intestinal tumors in rats by piroxicam," *Cancer Res.*, 49:6471–6473, 1989.

Rao et al., "Chemoprevention of colon carcinogenesis by sulindac, a nonsteroidal anti–inflammatory agent," *Cancer Res.*, (55):1464–1472, 1995.

Reddy et al., "Chemoprevention of colon carcingensis by concurrent administration of piroxicam, a nonsteroidal anti–inflammatory drug with D,L–α–difluoromethylornithine, and ornithine decarboxylase inhibitor, in diet," *Cancer Res.*, (50):2562–2568, 1990.

Samaha et al., "Modulation of apopotsosi by sulindac, curcumin, phenylethyl–3–methylcaffeate, and 6–phenylhexyl isothiocyanate, apoptotic index as a biomarker in colon cancer chemoprevention and promotion," *Cancer Res.*, (57):1301–1305, 1997.

(List continued on next page.)

Primary Examiner—Jerome D. Goldberg
(74) *Attorney, Agent, or Firm*—Fulbright & Jaworski

(57) ABSTRACT

Activation of the Ki-ras proto-oncogene is common in colon carcinogenesis. Non-steroidal anti-inflammatory drugs (NSAIDs) inhibit carcinogen-induced colon carcinogenesis, decrease the frequency of Ki-ras mutations in the azoxymethane-treated rat model, and induce apoptosis in a variety of cell types. Sulindac, as well as other non-steroidal anti-inflammatory agents, are provided in combination with DFMO the prevention and/or treatment of cancers characterized by the expression of an activated Ki-ras. Provided with the present invention are pharmaceutically acceptable compositions that include a non-steroidal anti-inflammatory agent, sulindac, together with an effective amount of difluoromethylornithine.

21 Claims, 11 Drawing Sheets

OTHER PUBLICATIONS

Su et al., "Multiple intestinal neoplasia caused by a mutation in the murine homolog of the APC gene," *Science*, (256):668–670, 1992.

Kelloff et al., "Chemopreventive drug development: perspectives and progress," *Cancer Epidemiology, Biomarkers and Prevention*, 3:85–98, 1994.

Thompson et al., "Inhibition of mammary carcinogenesis by sulfone metabolite of sulindac," *J. Natl. Cancer Inst.*, (87):125–1260, 1995.

Kelloff et al., "New agents for cancer chemoprevention," *J. Cell. Biochem.*, 265:1–28, 1996.

Kelloff et al., "Perspectives on chemoprevention agent selection and short term clinical prevention trials," *European J. Cancer Prevention*, 5(Supp. 2):79–85, 1996.

Boone and Kelloff, "Biomarker end–points in cancer chemoprevention trials," In: *Application of Biomarkers in Cancer Epidemiology*, Toniola et al., eds, 273–280, 1997.

Arber et al., "A K–ras oncogene increases resistance to sulindac–induced apoptosis in rat enterocytes," *Gastroenterology*, (113):1892–1990, 1997.

Braverman et al., Ornithine decarboxylase: an unreliable marker for the identification of population groups at risk for colonic neoplasia, *Am. J. Gastronenterology*, 85:723–726, 1990.

Pasricha et al., "The effects of sulindac on colorectal proliferation and apoptosis in familial adenomatous polyposis," *Gastroenterology*, 109:994–998, 1995.

Porter et al., "Polyamine biosynthetic activity in normal and neoplastic human colorectal tissue," *Cancer*, 60:1275–1281, 1987.

Boone et al., "Biomarker end–points in cancer chemoprevention trails," *IARC Scientific Publications*, 142:273–280, 1997.

Kelloff et al., "Chemopreventive drug development: perspectives and progress," *Cancer Epidemiology Biomarks and Prevention*, 3:85–98, 1994.

Kelloff et al., "New agents for chemoprevention," *J. of Cell. Biochemistry*, 63:1–28, 1996.

Kelloff et al., "Perspectives on chemoprevention agent selection and short–term clinical prevention trials," *European J. of Cancer Prevention*, 5:79–85, 1996.

DFMO AND SULINDAC COMBINATION IN CANCER CHEMOPREVENTION

This application claims the benefit of U.S. Provisional Application, Ser. No. 60/079,850, filed Mar. 28, 1998. The government owns rights in the present invention pursuant to grant number CA-72008 from the National Institutes of Health.

BACKGROUND OF THE INVENTION

1. Field of the Invention

The present invention relates generally to the fields of cancer biology and biochemistry. More particularly, the present invention is directed to a method of cancer chemotherapy in mammals.

2. Description of Related Art

Mutational activation of the Kirsten (Ki)-ras oncogene is an important genetic alteration in colorectal neoplasia. Ki-ras mutations have been detected in approximately 50 percent of sporadic human colorectal tumors (Vogelstein et al., 1988; Burmer and Loeb, 1989). Ki-ras mutations have been detected in aberrant crypt foci, as well as in adjacent regions of histologically normal mucosa (Losi et al., 1996). These findings suggest that the mutation of Ki-ras may be a relatively early event in the temporal development of colon cancer. Ki-ras also is mutated in chemically-induced rodent tumors, such as the azoxymethane (AOM)-treated rat model, with a frequency similar to that of human cancers (Erdman, 1997; Vivona et al., 1993). Although the role of Ki-ras in tumorigenesis is unclear, activation of this gene has been correlated with deficient apoptosis in human colorectal neoplasms (Ward et al., 1997).

The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. NSAIDs also inhibit the development of tumors harboring an activated Ki-ras (Singh and Reddy, 1995). NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, is a function of their ability to inhibit prostaglandin synthesis (reviewed in DuBois et al., 1996; Lupulescu, 1996; Vane and Botting, 1997). Recent studies, however, indicate that NSAIDs may act through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a).

Several NSAIDs have been examined for their effects in human clinical trials. A phase IIa trial (one month) of ibuprofen was completed and even at the dose of 300 mg/day, a significant decrease in prostoglandin $E_2$ ($PGE_2$) levels in flat mucosa was seen. A dose of 300 mg of ibuprofen is very low (therapeutic doses range from 1200–3000 mg/day or more), and toxicity is unlikely to be seen, even over the long-term. However, in animal chemoprevention models, ibuprofen is less effective than other NSAIDs. Studies have suggested a beneficial effect of the NSAID, aspirin, on colon cancer incidence, with effects being evident only at a weekly total dose of 1000 mg or greater (Giovannucci et al., 1996). However, three large cohort studies have produced conflicting reports on the beneficial effect of aspirin (Gann et al., 1993; Giovannucci et al., 1996; Greenberg et al., 1993). One group of investigators has recently shown that $PGE_{2\alpha}$ can be decreased at a dose between 80 and 160 mg/day. In contrast, another group of investigators have shown no such effect on colon mucosal prostaglandins at these low doses of aspirin, although substantial education of prostaglandins in upper gastrointestinal mucosa was demonstrated. The results of these studies indicate that a dose of aspirin of 80 mg is at the threshold of effect of this agent on colon mucosa.

The NSAID piroxicam is the most effective chemoprevention agent in animal models (Pollard and Luckert, 1989; Reddy et al., 1987), although it demonstrated side effects in a recent IIb trial. A large meta-analysis of the side effects of the NSAIDs also indicates that piroxicam has more side effects than other NSAIDs (Lanza et al., 1995). Sulindac has been shown to produce regression of adenomas in Familial Adenomatous Polyposis (FAP) patients (Muscat et al, 1994), although at least one study in sporadic adenomas has shown no such effect (Ladenheim et al., 1995).

The importance of Ki-ras activation in NSAID-mediated chemoprevention has not yet been determined. NSAIDs induce apoptosis in both colon tumor cell lines and animal tissues, and appear to inhibit Ki-ras activation in tumors, however the activation of Ki-ras has not yet been investigated as a mechanism of NSAID-mediated cytotoxicity. It also is not known if such cytotoxicity is dependent on the anti-inflammatory properties of the NSAIDs. The NSAID sulindac, which also inhibits Ki-ras activation, is metabolized to two different molecules which differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis.

$\alpha$-Difluoromethylornithine (DFMO) is an enzyme-activated, irreversible inhibitor of ornithine decarboxylase (ODC) and causes depletion in the intracellular concentrations of putrescine and its derivative, spermidine (Pegg, 1988). Levels of spermine, which is derived from spermidine, are not as markedly affected by the enzyme inhibition. DFMO was initially synthesized for therapeutic anticancer usage, but it was found not to be an active cytotoxic agent in chemotherapy trials against human cancer (McCann and Pegg, 1992), except perhaps demonstrating moderate activity in the treatment of malignant brain tumors (Levin et al., 1987). In general, the compound was nontoxic, with the significant exception of hearing loss, which was reversible after the drug treatment was discontinued (Meyskens et al., 1986). The onset of the hearing loss could be associated with total cumulative dose (Croghan et al., 1991).

In experimental animal models, DFMO is a potent inhibitor of carcinogenesis that is especially active in preventing carcinogen-induced epithelial cancers of many organs, including those of the colon (Weeks et al., 1982; Thompson et al., 1985; Nowels et al., 1986; Nigro et al., 1987). DFMO acts late in the tumor-promotion phase in animals, but the precise mechanism by which it inhibits the development of polyps and cancers is unknown. Effects on cell transformation, invasion, and angiogenesis by ornithine decarboxylase and polyamines have been reported (Auvinen, 1997); for example, overexpression of ODC enhances cellular transformation and invasion (Kubota et al., 1997).

The combination of DFMO and piroxicam has been shown to have a synergistic chemopreventive effect in the AOM-treated rat model of colon carcinogenesis (Reddy et al., 1990), although DFMO exerted a greater suppressive effect than piroxicam on Ki-ras mutation and tumorigenesis when each agent was administered separately (Singh et al., 1993; Reddy et al., 1990; Kulkami et al., 1992). In one study, administration of DFMO or piroxicam to AOM-treated rats reduced the number of tumors harboring Ki-ras mutations from 90% to 36% and 25% respectively (Singh et al., 1994). Both agents also reduced the amount of biochemically active p21 ras in existing tumors. (Singh et al., 1993).

There remains a need for effective and less toxic methods for treating cancers. Current treatment protocols, especially those for colon cancers and polyps, include tumor resection, chemotherapy and radiation therapy. Colorectal cancer is the second leading cause of death from cancer in The United States.

SUMMARY OF THE INVENTION

Accordingly, it is the object of the present invention to provide a novel method for preventing and/or treating cancer in a patient having an Ki-ras-dependent cancer comprising administering an effective amount of difluoromethylomithine (DFMO) in combination with sulindac.

It is another object of the present invention to provide a novel method for preventing and/or treating cancer in a patient comprising administering a dose of DFMO of about 0.05 to about 5.0 gm/M 2/day, and preferably 0.05 to about 0.50 gm/M$^2$/day and a dose of sulindac of about 10 to 1500 mg/day, and preferably 10 to 400 mg/day.

It is another object of the present invention to provide a novel method for preventing and/or treating cancer in a patient, wherein the cancer is colon cancer, breast cancer, pancreatic cancer, brain cancer, lung cancer, stomach cancer, a blood cancer, skin cancer, testicular cancer, prostate cancer, ovarian cancer, liver cancer, esophageal cancer, familial adenomatous polyposis.

It is another object of the present invention to provide a novel method for preventing and/or treating cancer in a patient having an Ki-ras-dependent cancer comprising administering an effective amount of difluoromethylornithine (DFMO) in combination with sulindac to said patient wherein DFMO is administered prior to sulindac, wherein DFMO is administered after sulindac, wherein DFMO is administered at the same time as sulindac, wherein DFMO is administered at least a second time, or wherein sulindac is administered at least a second time.

It is another object of the present invention to provide a novel method for preventing and/or treating cancer in a patient, following resection of a solid tumor,wherein DFMO and sulindac are admininstered prior to said resection or are admininstered after said resection.

It is another object of the present invention to provide a novel method for preventing and/or treating cancer in a patient, wherein the DFMO and sulindac are administered directly to said tumor, are administered systemically, are administered into the regional vasculature of said tumor, are administered into the region lymph system of said tumor, or are administered by different routes.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8. The effect of DFMO on apoptosis induced by sulindac sulfone in Caco-2 parental or Ki-ras transfected cells. Caco-2 cells (8A) or Caco-2 Ki-ras clone 60 (8B) were seeded in the presence or absence of 5 mM α-difluoromethylornithine (DFMO) with or without 600 mM sulindac sulfone (SN). Cells were grown over a period of 6 days. Cells were harvested at various days (0, 2, 4 and 6 days), spun onto slides and stained. Apoptosis was determined by light microscopy. Percentage of apoptotic cells was calculated as the number of apoptotic cells out of the total cells counted times 100. At least 500 cells were counted for each sample.

DESCRIPTION OF ILLUSTRATIVE EMBODIMENTS

Figure 1:
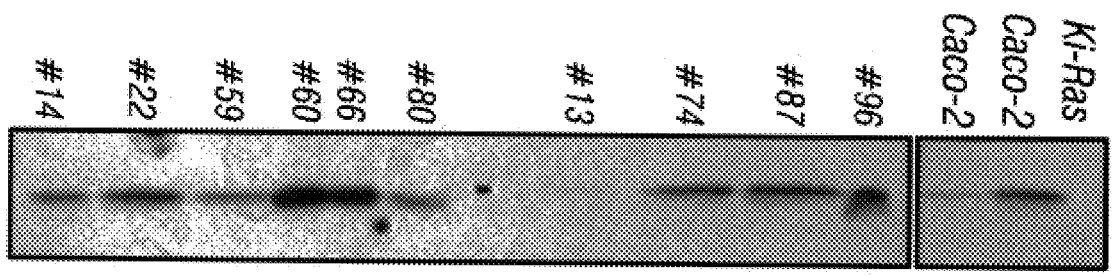
FIG. 1. Ki-ras transfection of Caco-2 human colon adenocarcinoma cells. Caco-2 cells were transfected with a plasmid directing the overexpression of an activated Kirsten-ras gene and subject to drug-resistance selection and clone. Detection of Ki-ras expression in various transfected clones by western blot, utilizing an antibody which detects both normal and activated p21$^{K-ras}$K. Numbered lanes refer to clonal isolates of transfected cells; Caco-2, untransfected parental cells; Caco-2/Ki-ras, pooled clones.

There is a need for effective and less toxic methods for preventing and/or treating cancers. Current treatment protocols, especially those for colon cancers and polyps, includes tumor resection, chemotherapy and radiation therapy. Colorectal cancer is the second leading cause of death from cancer in The United States. During the last fifteen years, emphasis has been placed on identification of high risk patients and families and outline of appropriate surveillance regimens for normal and high risk patients for colorectal cancer. The present invention concerns the development of an effective and safe drug combination that will improve the prognosis of certain cancers. The present invention provides for the use of two inhibitors of colon carcinogenesis, DFMO and sulindac, which affect the same ras-dependent signaling pathway. When this pathway is disrupted, carcinogenesis is disrupted, leading to inhibiting the growth of the cancer cells, killing the cancer cell outright, inducing apoptosis, inhibiting metastasis, reducing overall tumor burden, inducing tumor regression, or any combination of these. This complementary action in the same pathway makes this combination more potent than either drug alone and better tolerated than either drug alone. This drug combination also serves to resolve a major problem in cancer, which is to prevent or effectively treat cancers without causing undue toxicity to patients.

I. Human Cancers

The present invention involves the delivery of therapeutic compounds to individuals to reduce or inhibit cancer cells. Target cancer cells include cancers of the lung, brain, prostate, kidney, liver, ovary, breast, skin, stomach, esophagus, head and neck, testicles, colon, cervix, lymphatic system and blood. Of particular interest are epithelial cancers of many organs, including those of the colon and polyps which tend to express an activated Ki-ras.

The present invention also involves the delivery of therapeutic compounds to individuals exhibitting pre-cancerous symptoms to prevent the onset of cancer. Cells of this catagory include polyps and other precancerous lesions, premalignancies, preneoplastic or other abarent phenotype indicating probable progression to a cancerous state.

1. Kirsten-Ras dependent cancers

Ras defines a protooncogene product that is found on chromosome 11. It is found in normal cells, where it helps to relay signals by acting as a switch (Lowy and Willumsen, 1993). When receptors on the cell surface are stimulated (by a hormone, for example), Ras is switched on and transduces signals that tell the cell to grow. If the cell-surface receptor is not stimulated, Ras is not activated and so the pathway that results in cell growth is not initiated. In about 30% of human cancers, Ras is mutated so that it is permanently switched on, telling the cell to grow regardless of whether receptors on the cell surface are activated or not. Point mutations in the cellular ras gene (c-ras) also can result in a mutant p21 protein that can transform mammalian cells.

Ras is a family of retrovirus-associated DNA sequences originally isolated from Harvey (H-ras, Ha-ras, rasH) and Kirsten (K-ras, Ki-ras, rasK) murine sarcoma viruses. Ras genes are widely conserved among animal species and sequences corresponding to both H-ras and K-ras genes have been detected in human, avian, murine, and non-vertebrate genomes. The closely related N-ras gene has been detected in human neuroblastoma and sarcoma cell lines. All genes of the family have a similar exon-intron structure and each encodes a p21 protein

2. Familial Adenomatous Polyposis, Syndrome, Gene

Familial Adenomatous Polyposis (FAP), an inherited polyposis syndrome, is the result of germ-line mutation of the adenomatous polyposis coli (APC) tumor suppresor gene (Su et al., 1992). This autosomal-dominant condition with variable expression is associated with the development of hundreds of colonic adenomas, which uniformly progress to adenocarcinoma by forty years of age, two decades earlier than the mean age diagnosis for sporadic colon cancer (Bussey, 1990). In prior studies of pre-symptomatic individuals with FAP, increased levels of the polyamines spermidine and spermine, and their diamine precursor putrescine, have been detected in normal-appearing colorectal biopsies when compared to normal family member controls (Giardiello et al., 1997). The activity of ornithine decarboxylase (ODC), the first and rate-limiting enzyme in mammalian polyamine synthesis, also is elevated in apparently normal colonic mucosal biopsies from FAP patients (Giardiello et al., 1997; Luk and Baylin, 1984). These findings are of interest as the polyamines are necessary for optimal cell proliferation (Pegg, 1986). Further, suppression of ODC activity, using the enzyme-activated irreversible inhibitor DFMO, inhibits colon carcinogenesis in carcinogen-treated rodents (Kingsnorth et al., 1983; Tempero et al., 1989).

The Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death.

II. Difluromethylornithine (DFMO)

DFMO, also know as eflornithine, has the following chemical designation; 2(Difluoromethyl)-DL-ornithine. It is an inhibitor of ornithine decarboxylase, the rate limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents.

In recent years, chemotherapeutic agents that directly inhibit polyamine synthesis have been developed. Difluoromethylornithine (DFMO), one such drug, is an irreversible inhibitor of ODC and potentially can be given continuously with significant anti-tumor effects. This drug is relatively non-toxic at low doses of 0.4 $gr/M^2/day$ to humans while producing inhibition of putrescine synthesis in tumors. Studies in a rat-tumor model demonstrate that DMFO infusion can produce a 90% decrease in tumor putrescine levels without suppressing peripheral platelet counts.

Side effects observed with DFMO include effects on hearing at high doses of 4 $gr/M^2/day$ that resolve when it is discontinued. These effects on hearing are not observed at lower doses of $0.4gr/M^2/day$ when administered for up to one year (Meyskens et al., 1994). In addition a few cases of dizziness/vertigo are seen that resolve when the drug is stopped. Thrombocytopenia has been reported predominantly in studies using high "therapeutic" doses of DFMO (>1.0 $g/m^2/day$) and primarily in cancer patients who had previously undergone chemotherapy or patients with compromised bone marrow. Although the toxicity associated with DFMO therapy are not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. DFMO may inhibit proliferative repair processes, such as epithelial wound healing.

Although DFMO can effectively block tumor putrescine biosynthesis, the resultant antitumor effect is cytostasis and not cytotoxicity. For example, DFMO reduces the growth rate of an MCA sarcoma but does not produce tumor regression. This finding is consistent with reports of other investigators who showed that DFMO is a cytostatic agent. However, studies indicate that a significant role exists for DFMO agents, permitting the future development of combination chemotherapeutic regimens which incorporate DFMO.

DFMO and its use in the treatment of benign prostatic hypertrophy are described in two patents, U.S. Pat. Nos. 4,413,141, and 4,330,559. U.S. Pat. No. 4,413,141 describes DFMO as being a powerful inhibitor of ODC, both in vitro and in vivo. Administration of DFMO causes a decrease in putrescine and spermidine concentrations in cells in which these polyamines are normally actively produced. Additionally, DFMO has been shown to be capable of slowing neoplastic cell proliferation when tested in standard tumor models. U.S. Pat. No. 4,330,559 describes the use of DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally, or parenterally.

The initial promise of DFMO as a therapeutic ODC inhibitor for use in the treatment of various neoplasias has dimmed somewhat because, although DFMO does, in fact, irreversibly inhibit ODC activity, cells treated in vivo with DFMO significantly increase their uptake of exogenous putrescine as described in U.S. Pat. No. 4,925,835. The intercellular transport mechanisms of the cell do an "end run" around the DFMO-impaired ODC activity by importing putrescine from the extra-cellular milieu. Therefore, DFMO's effect in vivo is far poorer than in vitro. So, while DFMO treatment effectively inhibits intracellular putrescine neogenesis, it also results in increased uptake of extracellular putrescine, thereby offsetting its ODC inhibitory effect.

This problem is compounded by the fact that putrescine is present in many common foods, such as orange juice, which contains approximately 400 ppm putrescine. This makes it virtually impossible to provide a patient a nutritionally sufficient diet which is free of putrescine. Therefore, DFMO-treated cells are capable of importing sufficient amounts of extracellular putrescine to support cell division.

Another drawback to DFMO is that, although it is a small molecule, it is relatively expensive to synthesize. The need for fluorination of a starting material or intermediate requires increased safety precautions and equipment which makes DFMO compounds difficult to synthesize at low cost.

However, because DFMO is an effective inhibitor of ODC, some researchers are attempting to use DFMO as part of a conjunctive treatment in combination with other therapeutic agents. For instance, U.S. Pat. No. 4,499,072, describe improving the polyamine-depletion effects of ODC inhibitors (including DFMO) by using interferon in combination with the ODC inhibitor. Additionally, it describes the use of both an ODC inhibitor and interferon in conjunction with a known cytotoxic agent such as methotrexate. U.S. Pat. No. 5,002,879, describe a similar conjunctive therapy in which an ODC inhibitor, preferably DFMO, is used in combination with lymphokine-activated killer (LAK) cells and interleukin-2.

Alternative stratagies to make DFMO more acceptable to human patients are described in U.S. Pat. No. 4,859,452. Formulations of DFMO are described which include essential amino acids in combination with either arginine or ornithine to help reduce DFMO-induced toxicities.

III. NSAIDs

NSAIDs are anti-inflammatory agents that are not steroids. In addition to anti-inflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. (AMA Drug Evaluations Annual, 1994, p 1814–5)

1. Sulindac and its major metabolites, sulindac sulfone and sulindac sulfide

Figure 11:
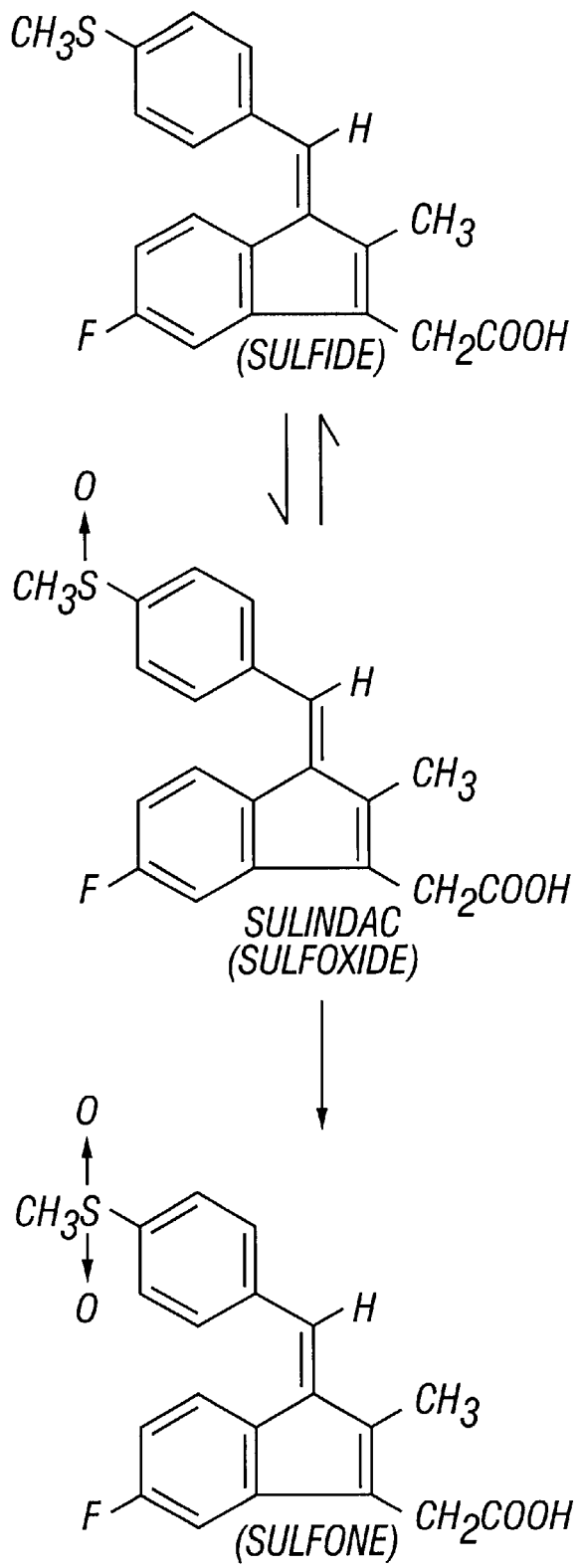
FIG. 11. Structural formulas of sulindac and its metabolites, sulindac sulfide and sulindac sulfone.

Sulindac is a non-steroidal, anti-inflammatory indene derivative with the following chemical designation; (Z)-5-Fluoro-2-methyl-1-((4 (methylsulfinyl)phenyl)methylene) 1H-indene-3-acetic acid (Physician's Desk Reference, Medical Economics Data, Montville, N.J., 1745–1747, 1999). The sulfinyl moiety is converted in vivo by reversible reduction to the sulfide metabolite and by irreversible oxidation to the sulfone metabolite (FIG. 11). Available evidence indicates that the sulfide derivative is the biologicaly activite compound. Based on this, sulindac is defined as a prodrug, and appears to be inactive or relatively weak in many tests where little or no metabolism can occur. Sulindac (Clinoril®) is available as 150- and 200-mg tablets. The most common dosage for adults is 150 to 200 mg twice a day, with a maximal daily dose of 400 mg. After oral administration, about 90% of the drug is absorbed. Peak plasma levels are achieved in about 2 hours in fasting patients and 3 to 4 hours when administered with food. The mean half-life of sulindac is 7.8 hours: the mean half-life of the sulfide metabolite is 16.4 hours. U.S. Pat. Nos. 3,647,858 and 3,654,349 cover preperations of sulindac.

Sulindac is currently indicated for the acute and long-term relief of signs and symptoms of osteoarthritis, rheumatoid arthritis, ankylosing spondylitis, acute gout, and acute painful shoulder. The analgesic and antiinflamatory effects exerted by sulindac (400 mg per day) are comparable to those achieved by aspirin (4 g per day), ibuprofin (1200 mg per day), indomethacin (125 mg per day), and phenylbutazone (400 to 600 mg per day). Side effects of sulindac include mild gastrointestinal effects in nearly 20% of patients, with abdominal pain and nausea being the most frequent complaints. CNS side effects are seen in up to 10% of patients, with drowsiness, headache, and nervouseness being those most frequently reported. Skin rash and pruritus occur in 5% of patients. Chronic treatment with sulindac can lead to serious gastrointestinal toxicity such as bleeding, ulceration, and perforation.

The potential use of sulindac for chemoprevention of cancers, and in particular colorectal polyps, has been well studied. Two recent U.S. Pat. Nos. 5,814,625 and 5,843,929, detail potential chemopreventive uses of sulindac in humans. Doses of sulindac claimed in U.S. Pat. No. 5,814,625 range from 10 mg to 1500 mg per day, with prefered doses of 50 mg to 500 mg per day. However, at the higher doses, the biggest problem with the use of sulindac as a single agent in chemoprevention is its well-known toxicities and moderately high risk of intolerance. The elderly appear to be especially vulnerable, as the incidence of side effects is higher in those over the age of 60. It is noted that this age group is most likely to develop colorectal cancer, and therefore, most likely to benefit from chemoprevention.

2. Piroxicam

A non-steroidal anti-inflammatory agent that is well established in the treatment of rheumatoid arthritis and osteoarthritis with the following chemical designation; 4-Hydroxy-2-methyl-N-2-pyridyl-2H1,2-benzothiazine-3-carboxamide 1,1-dioxide. Its usefulness also has been demonstrated in the treatment of musculoskeletal disorders, dysmenorrhea, and postoperative pain. Its long half-life enables it to be administered once daily. The drug has been shown to be effective if administered rectally. Gastrointestinal complaints are the most frequently reported side effects.

3. Aspirin

The prototypical analgesic used in the treatment of mild to moderate pain. It has anti-inflammatory and antipyretic properties and acts as an inhibitor of cyclooxygenase which results in the inhibition of the biosynthesis of prostaglandins. Aspirin also inhibits platelet aggregation and is used in the prevention of arterial and venous thrombosis. (From Martindale, The Extra Pharmacopoeia, 30th ed, p5)

4. Indomethacin

A non-steroidal anti-inflammatory agent that is used in the treatment of osteoarthritis, acute gouty arthritis, rheumatoid arthritis, and ankylosing spondylitis. Due to its action as a prostaglandin synthase inhibitor, indomethacin has also been used to delay premature labor.

5. Combinations of NSAIDs

Combinations of various NSAIDs are also used for various purposes. By using lower doses of two or more NSAIDs, it is possible to reduce the side effects or toxicities associated with higher doses of individual NSAIDs. Specifically for the purposes outlined in this invention, sulindac can be used in combination with other NSAIDs in this manner.

IV. Routes of Administration and Formulation

According to the present invention, one may treat a patient by direct injection of a tumor or its vasculature with the therapeutic compounds. Alternatively, the tumor may be infused or perfused with the therapeutic compounds using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 wk or longer following the initiation of treatment. Generally, the dose of the therapeutic composition via continuous perfusion will be equivalent to that given by a single or multiple injections, adjusted over a period of time during which the perfusion occurs.

An exemplary course of treatment, for a primary tumor or a post-excision tumor bed, could involve multiple doses. During a course of treatment, the need to complete the planned dosings may be re-evaluated. Various combinations of DFMO and sulindac may be employed, either used sequentially or simultaneously. For instance, where DFMO is "A" and the sulindac is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

The time between treatment of sulindac and DFMO may be for a period from about 1–2 hours, to about 2–6 hours, to about 6–12 hours, to about 12–24 hours, to about 1–2 days, to about 1–2 wk or longer following the initiation of treatment. Alternatively, simultaneous administration of DFMO and sulindac, with or without sequential administration of either DFMO or sulindac could also be employed. For instance where DFMO is "A" and the sulindac is "B" and "AB "is both together:

AB/A A/AB B/AB AB/B AB/AB AB/AB/AB

AB/A/A AB/B/B AB/A/B AB/B/A

A/AB/B A/AB/A B/AB/B B/AB/A

A/B/AB A/A/AB B/B/AB B/A/AB

AB/AB/A AB/AB/B AB/A/AB AB/B/AB A/AB/AB B/AB/AB

Results of the therapeutic treatments described above using the combination of DFMO and sulindac on patients with tumors can vary. The therapy may inhibit the growth of the cancer cells, kill the cancer cell outright, induce apoptosis, inhibit metastasis, reduce overall tumor burden, induce tumor regression, or any combination of these. Any and all of these results are adventageous to the patient.

Aqueous compositions of the present invention comprise an effective amount of the therapeutic compound, further dispersed in pharmaceutically acceptable carrier or aqueous medium. The phrases "pharmaceutically or pharmacologically acceptable" refer to compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

Solutions of therapeutic compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Where clinical application of liposomes containing therapeutic compounds is undertaken, it will be necessary to prepare the liposome complex as a pharmaceutical composition appropriate for the intended application. Generally, this will entail preparing a pharmaceutical composition that is essentially free of pyrogens, as well as any other impurities that could be harmful to humans or animals. One also will generally desire to employ appropriate buffers to render the complex stable and allow for uptake by target cells.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

The therapeutic compositions of the present invention may include classic pharmaceutical preparations. Administration of therapeutic compositions according to the present invention will be via any common route so long as the target tissue is available via that route. This includes oral, nasal, buccal, rectal, vaginal or topical. Topical administration would be particularly advantageous for treatment of skin cancers, to prevent chemotherapy-induced alopecia or other dermal hyperproliferative disorder. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, the preferred route is aerosol delivery to the lung. Volume of the aerosol is between about 0.01 ml and 0.5 ml. Similarly, a preferred method for treatment of colon-associated disease would be via enema. Volume of the enema is between about 1 ml and 100 ml.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i. e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Cell culture and drug treatments

Caco-2 cells were obtained from the American Type Culture Collection (Rockville, Md.). Caco-2 cells were maintained in Modified Eagle Media (GIBCO, Grand Island, N.Y.) supplemented with 10% fetal bovine serum and a 1% penicillin (10,000 units/ml)-streptomycin (10,000 mg/ml) solution (GIBCO, Grand Island, N.Y.). Transfected Caco-2 cells resistant to neomycin were maintained in 400 $\mu$g/ml G418. Cells were maintained at 37° in the presence of 5% $CO_2$ in air.

All cells were passed into new medium every two to three days, just prior to confluence. Drug additions were performed at the time of cell seeding and in MEM for each cell line unless otherwise noted. DFMO was provided by Marion Merrel Dow Company (Cincinnati, Ohio). The two metabolites of sulindac, sulindac sulfone and sulfide, were obtained from Cell Pathways, Inc. (Horsham Pa.).

Cell number and viability determinations

Caco-2 cells were removed from the monolayer by treatment with trypsin (1500 units/ml, Calbiochem, San Diego, Calif.)-EDTA (.7mM) and counted using a hemocytometer. A sample of the cell suspension was combined in a 1:1 volume ratio with trypan blue dye (GIBCO, Grand Island, N.Y.), and at least two independently prepared suspensions were counted on a hemocytometer, two counts each. For all cell types, viability was determined by the percentage of cells able to exclude the trypan blue dye.

Apoptosis Quantitation

Apoptosis was quantitated by morphological examination of cells on prepared slides. Each sample was prepared by pooling trypsinized cells with the aspirated culture medium and an additional saline wash of the tissue culture plate. Slides for light microscopy were prepared by placing 20,000 or 40,000 cells into a cytospin cup and pelleting the cells onto slides via centrifugation using a cytospin (Shandon Lipshaw, Pittsburgh, Pa.) at 600 r.p.m. for 2 min. Cells were affixed to the slides by immersion of the slide into 100% methanol for at least 1 min. Slides were stained using a 1:10 (for CHO cells) or a 1:20 (for Caco-2 cells) dilution of Modified Giemsa stain (Sigma Chemical Co., St. Louis, Mo.). Apoptotic cells were identified by characteristic chromatin condensation, cytoplasmic vacuole formation, cell shrinkage, and formation of apoptotic "bodies" (Kerr et al., 1994). Apoptotic bodies which were not enclosed by membranes were not included in the cell scoring. At least 500 cells were scored for each treatment for each day and frequencies were expressed as a percentage of the total cells counted.

Clonogenic Assays

Caco-2 cell survival was determined by colony-forming efficiency. Caco-2 cells or the Ki-ras-transfected clones were plated at a cell density of $2 \times 10^5$ cells per 60 mm dish in MEM, in the presence or absence of DFMO at varied concentrations. Cells were grown for 24 h, and then the DFMO media was removed. The plates were rinsed twice with saline, and MEM containing varied concentrations of sulindac sulfide or sulfone was added. Cells were grown for an additional 24 h, and then replated at 3 serially diluted concentrations, with 3 plates seeded for each concentration. Approximately 21 days later, the plates were stained for colony formation.

Plates were removed from the incubator and an equal volume of a 3:1 volume ratio of methanol and acetic acid was added to each plate for 5 min. The supernate was aspirated, and the colonies were stained by the addition of approximately 1 mL of crystal violet stain (5 mg/mL in 100% ethanol) (Sigma Chemical Co., St. Louis, Mo.). The plates were then rinsed in distilled water and air dried. Colonies were defined as consisting of a minimum of 50 cells, with each plate containing 20 or more colonies for inclusion in the data set. Standard deviations were prepared from data in which all 3 plates contained a sufficient number of colonies to be included.

Establishment and characterization of clones

A cDNA encoding an activated Ki-ras$^{Val12}$ was purchased from the American Type Culture Collection (Rockville, Md.). This cDNA was ligated into the multiple cloning site of a pCDNA3 mammalian expression vector (Invitrogen Corp., Carlsbad, Calif.), and vectors containing the Ki-ras insert were isolated according to standard protocols (Ausubel, 1995). Large-scale amounts of plasmid (mg quantities) suitable for mammalian cell transfection were purified using the Nucleobond Plasmid Kit (Clontech Laboratories, Inc., Palo Alto, Calif.).

The calcium phosphate transfection method was used to introduce the pCDNA3-Ki-ras plasmid into Caco-2 cells, according to established protocols (Ausubel, 1995). One week after transfection, geneticin (Life Technologies, Inc., Germantown, Md.) was added to the media at a concentration of 400 µg/ml. Stable clones were isolated with the use of trypsin soaked filter disks placed over isolated colonies on a tissue culture plate, and then transferred to the wells of a 48-well plate. Clones were maintained in 400 µg/ml of geneticin, and screened via western blot for Ki-ras expression.

Preparation of whole cell lysates of Caco-2 cells

Whole-cell lysates of Caco-2 cells were prepared according to commercially available protocols (Santa Cruz Biotechnology, Santa Cruz, Calif.). Plates were kept on ice, and cells were scraped off the tissue culture plates in the presence of RIPA buffer (PBS, 1% NP-40, .5% sodium deoxycholate, 0.1% sodium dodecylsulfate, 10 mg/ml PMSF, 30 µg/ml aprotinin, 100 mM sodium orthovanadate). The cell suspension was then passed twice through a 22-gauge needle, and was centrifuged at 10000×g for 20 min to clarify the lysate.

Western Blot

Characterization of Ki-ras expression in transfected Caco-2 clones was performed by western blot, using a mouse monoclonal antibody directed against both normal and activated Ki-ras (Santa Cruz Biotechnology, Santa Cruz, Calif.). Samples were electrophoresed onto a 12.5% acrylarnide gel, and the proteins were then transferred onto a Hybond nitrocellulose membrane (Amersham Life Science, Inc., Arlington Heights, Ill.). Samples were run at 50 V for 16 h in a transfer apparatus (Bio-Rad Laboratories, Hercules, Calif.) in transblot buffer (30% MeOH, 50 mM Tris, 191 mM glycine). The nitrocellulose membrane was blocked for one h in Blotto (TBS, 5% non-fat dry milk, 0.05% Tween-20) (Sigma Chemical Co., St. Louis, Mo.). A mouse monoclonal IgG directed against either Ki-ras or c-myc (Santa Cruz Biotechnology, Santa Cruz, Calif.) was diluted 1:100 in Blotto and applied to the membrane for 2 h. Membranes were washed in TTBS for 3 washes of 5 min each, and then a horse radish peroxidase (HRP)-conjugated goat anti-mouse IgG secondary antibody was diluted in Blotto and applied to the membrane. The membrane was incubated in secondary antibody for 1 h and then the membrane was washed again in TTBS. Visualization was made with the ECL Detection system (Amersharn Life Science, Inc., Arlington Heights, Ill.).

Protein gel electrophoresis.

SDS-polyacrylamide electrophoresis (PAGE) was performed according to the method of Laemmli (1970), except that bisacrylamide was replaced with NN'-diallyltartardiamide (Bio-Rad Laboratories, Hercules, Calif.). Samples were diluted in electrophoresis buffer (2% SDS/5% β-mercaptoethanol/3% sucrose in 300 mM Tris-HCl, pH 7.0) and heated at 100° for 5 min before loading on a 12.5% acrylamide gel.

Protein quantitation

Protein measurements of the lysates used for western blotting were performed with the DC protein assay kit (Bio-Rad Laboratories, Hercules, Calif.), using the modified method suitable for use with detergents. Protein concentrations for both assay types were estimated by comparing the absorbance of unknown samples to that of known bovine serum albumin standard concentrations in the same assay.

Results

Isolation and characterization of Caco-2 transfected cells

Caco-2 human colon adenocarcinoma cells were used to determine the effects of sulindac, and DFMO on cells containing an activated Ki-ras. Caco-2 cells are one of the few colon tumor lines which contain a normal Ki-ras gene (Delage et al., 1993; Trainer et al., 1988). These cells possess many of the characteristics of mature enterocytes, including spontaneous differentiation and hydrolase secretion (Rousset, 1986). Caco-2 cells were stably transfected with a plasmid directing the overexpression of an activated Ki-ras, and individual clones were subsequently isolated. Ten clonal populations were characterized by western blot employing an antibody that reacts with both normal and mutated Ki-ras proteins. (FIG. 1). Ki-ras protein was detectable in the parental cells, and was present in increased amounts in most of the transfectants. One clone, 13, had levels of Ki-ras below that of the parental Caco-2 cells, whereas clones 14, 22, 59, 80, 74, and 87 were intermediate expressors, and contained levels of Ki-ras similar to the uncloned Ki-ras transfected population (Caco-2/Ki-ras). Clones 60, 66, and 96 showed the highest level of expression. Clones 60 and 66 were utilized for further study.

Figure 2A:
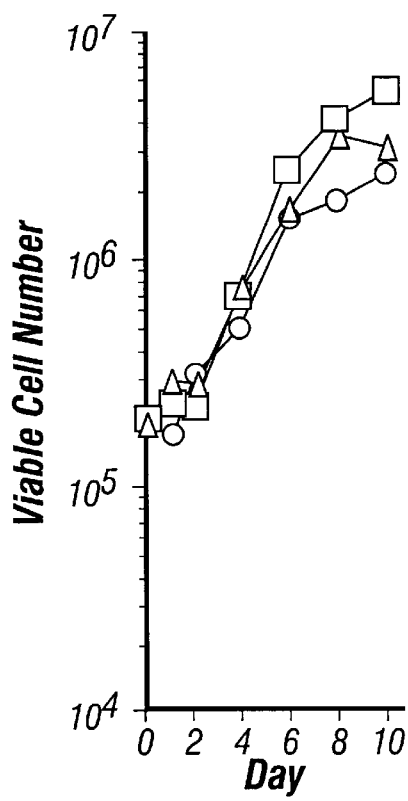
FIG. 2. Effect of sulindac sulfide and sulfone on the growth of Ki-ras transfected cells. Caco-2 parental cells (○), Ki-ras clone #60 (□), and Ki-ras clone #66 (Δ) were seeded in the presence of vehicle (A), 120 μM sulindac sulfide (B), or 600 μM sulindac sulfone (C) and harvested at 2-day intervals. Viable cell number was determined by trypan blue dye exclusion.
Figure 2B:
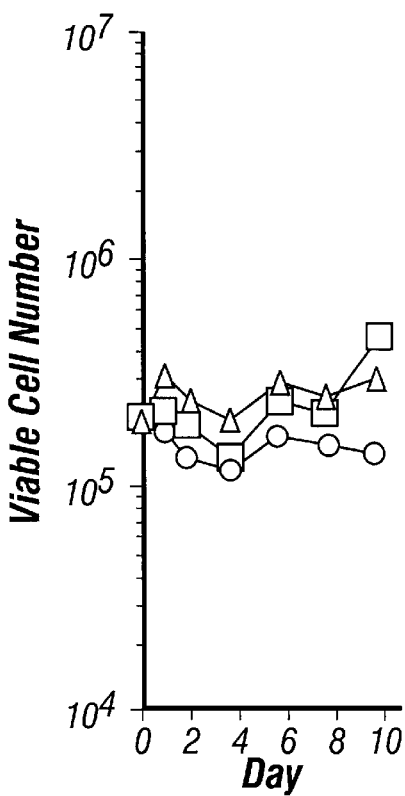
Figure 2C:
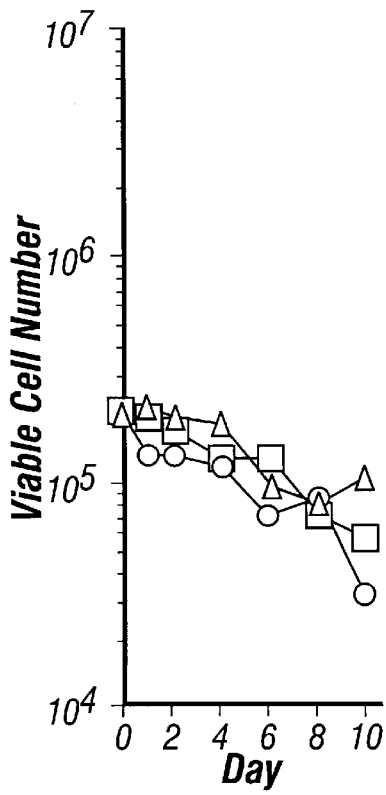

Effect of sulindac sulfone and sulfide on growth of cells expressing an activated Ki-ras Growth of parental Caco-2 cells as well as clones 60 and 66 were measured in the presence of vehicle, 120 $\mu$M sulindac sulfide, or 600 $\mu$M sulindac sulfone (FIG. 2). In the presence of vehicle only (2A), the expression of activated Ki-ras did not confer a growth advantage to either transfected cell line. The number of viable cells in all sulfide-treated cultures remained relatively unchanged throughout the 10-day growth period (2B), whereas treatment of cultures with the sulfone derivative resulted in a pronounced cell loss beginning 6 days after treatment (2C). Ki-ras activation did not confer a selective toxicity in the presence of either sulindac metabolite.

Effect of Ki-ras on apoptosis induced by sulindac sulfide or sulfone.

Figure 3A:
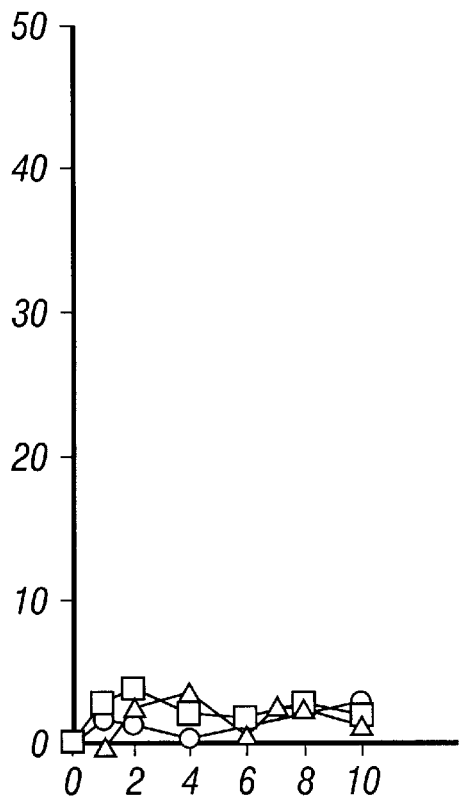
FIG. 3. Induction of apoptosis by sulindac sulfide and sulfone in Ki-ras-transfected cells. Caco-2 parental cells (○), Ki-ras clone #60 (□), and Ki-ras clone #66 (Δ) were seeded in the presence of vehicle (A), 120 μM sulindac sulfide (B), or 600 μM sulindac sulfone (C) and harvested at 2-day intervals. Apoptosis was determined by light microscopy.
Figure 3B:
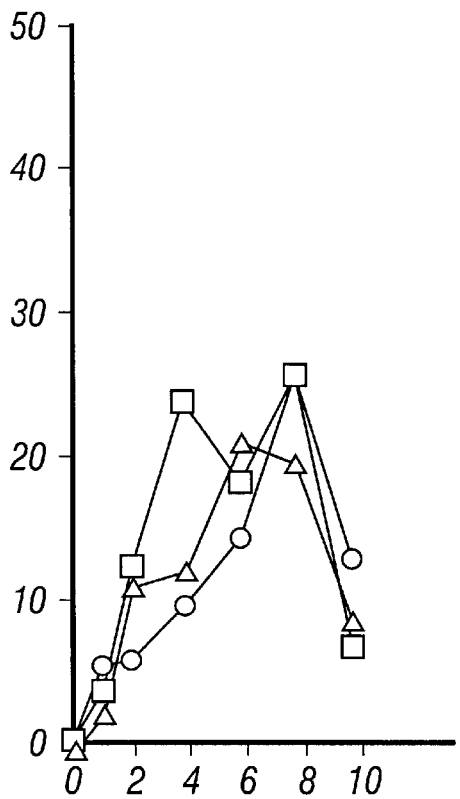
Figure 3C:
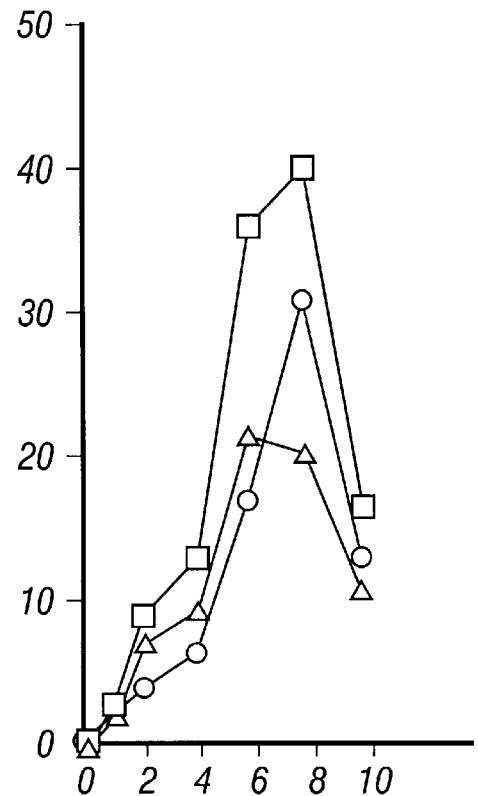

Sulindac has been shown to cause apoptosis in the AOM-treated rodent model. In this model, sulindac also reduces the number of tumors harboring an activated Ki-ras, which suggests that apoptosis may occur by a Ki-ras dependent mechanism. To test this hypothesis, Caco-2 parental cells and clones 60 and 66 were treated with vehicle (FIG. 3A), 120 $\mu$M sulindac sulfide FIG. (3B), or 600 $\mu$M sulindac sulfone FIG. (3C) and apoptosis of each culture was quantitated by light microscopy. The percentage of cells undergoing apoptosis in response to vehicle alone were minimal, with a peak apoptosis index of 4 percent FIG. (3A). Caco-2 parental cells exposed to sulfide displayed a gradual increase in apoptosis which peaked at 8 days in culture. Clone 60 cells, and to a lesser extent, clone 66, displayed an earlier onset of apoptosis. Clone 60 reached peak apoptosis levels at day 4 compared to day 8 of the parental cells, while clone 6 reached a peak level of apoptosis by day 6. In both the Caco-2 parental and clone 60 cells, induction of apoptosis by sulindac sulfone was more pronounced than with the sulfide FIG. (3C). Upon exposure to the sulfone, clone 60 cells reached a peak level of apoptosis by day 6, compared to day 8 in the parental cells. Ki-ras appears to accelerate the onset of apoptosis in response to both sulindac sulfone and sulfide.

Figure 4A:
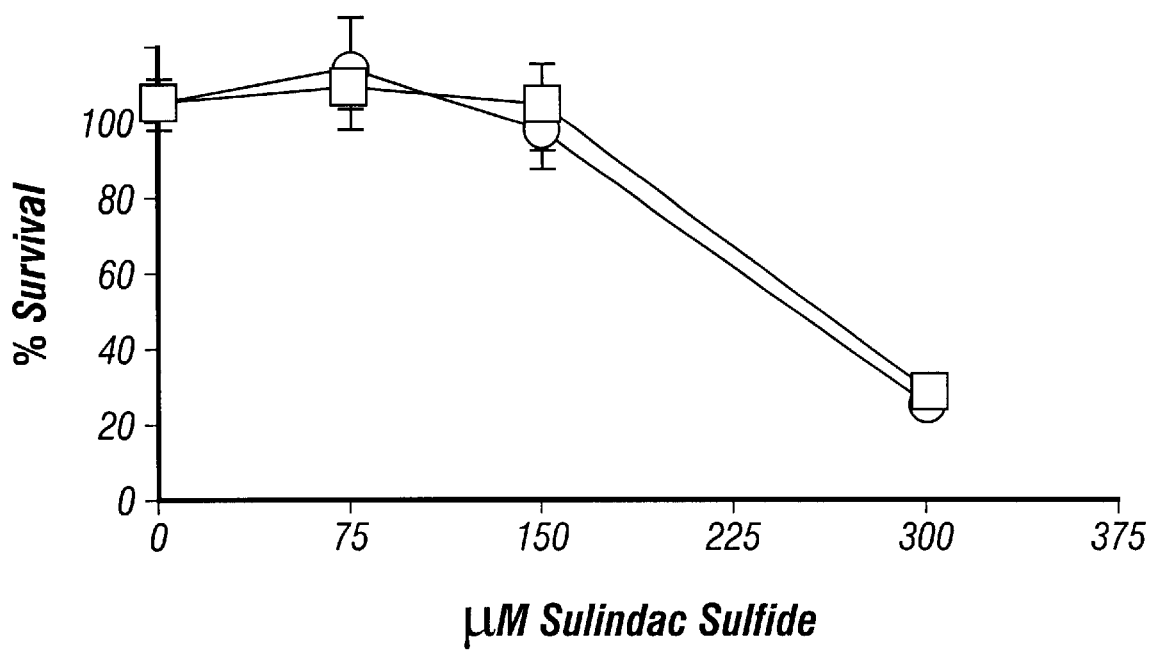
FIG. 4. Survival of Caco-2 parental or Ki-ras clone #60 cells in sulfide or sulfone. Caco-2 parental cells (○) and Ki-ras clone #60 (□) were treated for 24 h with increasing concentrations of sulindac sulfide (0, 75, 150, and 300 μM) (A) or sulindac sulfone (0, 300, 600 and 1200 μM) (B). Cells were replated at diluted concentrations in the absence of drug and grown for 21 days. Plates were stained with crystal violet and the number of colonies on each plate was determined. Plating efficiency was determined by dividing the number of colonies by the total number of cells plated. These numbers were then normalized to the plating efficiency of non-drug-treated controls of the same line. Data points without error bars contain a standard deviation too small to be represented.
Figure 4B:
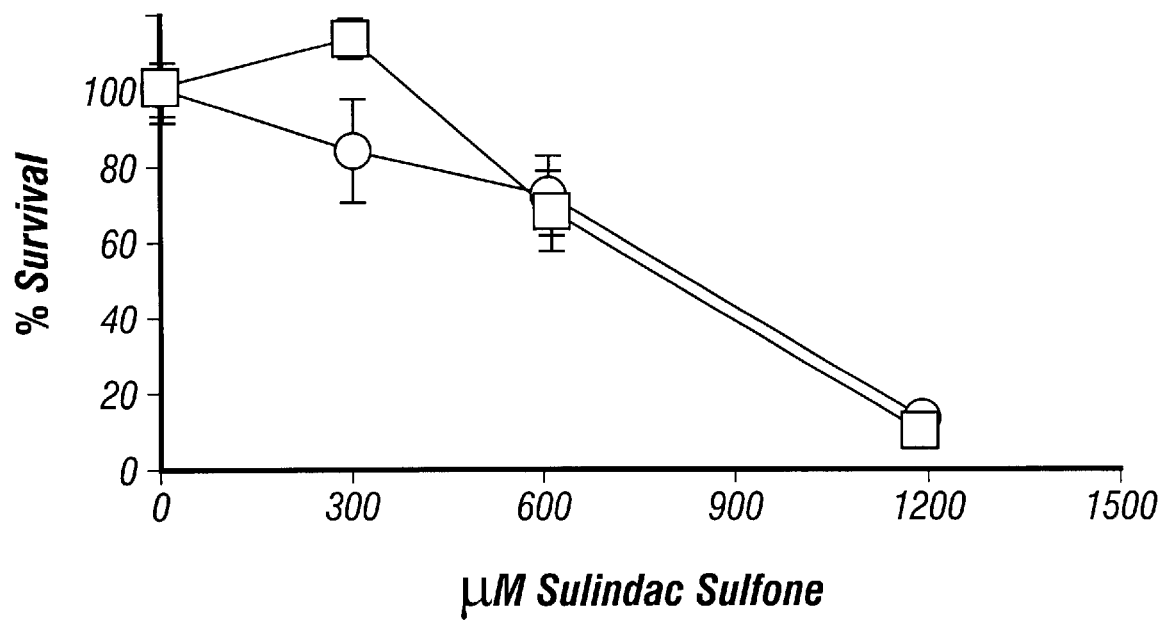

Effect of Ki-ras activation on the survival of cells exposed to sulindac sulfide or sulfone In an effort to better characterize the apoptosis response to the sulindac metabolites in cells with an activated Ki-ras, the colony-forming efficiencies of Caco-2 and clone 60 cells were measured after exposure to increasing concentrations of sulindac sulfide or sulfone (FIG. 4). Cells were treated for 24 hr and then replated at diluted concentrations in fresh media. By this method, a 50% decrease in cell number occurred at approximately 225 $\mu$M sulindac sulfide and 800 $\mu$M sulindac sulfone. The expression of an activated Ki-ras did not affect the final measure of viability caused by either sulindac metabolite, as the transfected cells displayed the same toxicity as the parental cells. Activation of Ki-ras was unable to confer a selective cytotoxicity in the presence of either sulindac metabolite.

Figure 5A:
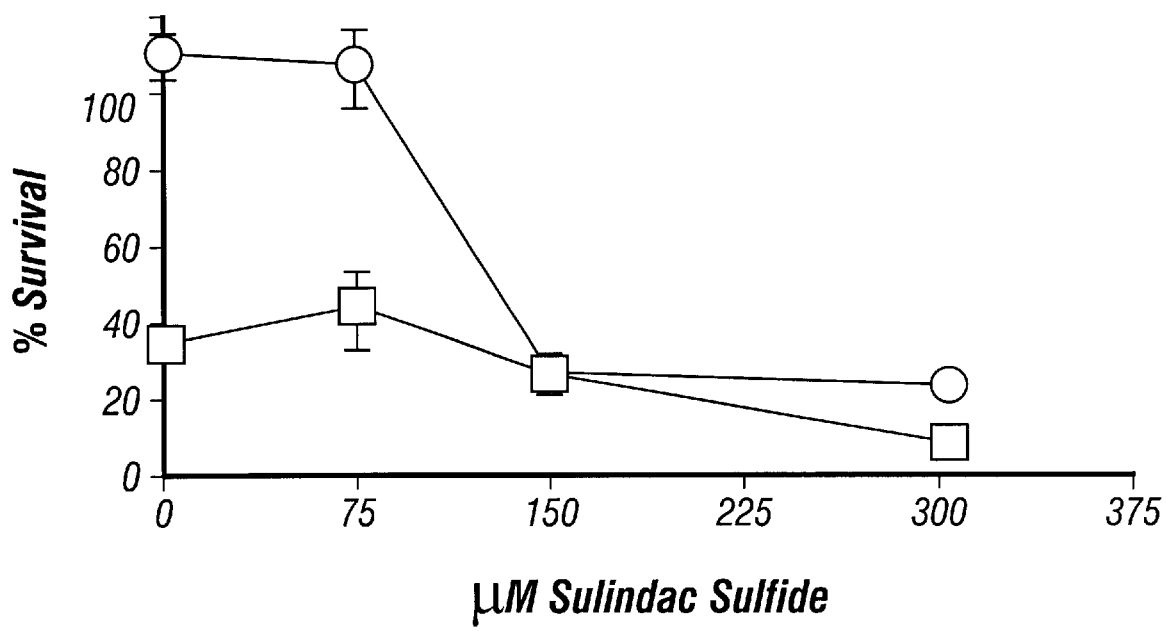
FIG. 5. Effect of DFMO on survival of Caco-2 parental or Ki-ras clone #60 cells in sulindac sulfide or sulfone. Caco-2 parental (●) or Ki-ras clone #60 (■) cells were treated for 24 h with 5 mM DFMO, and then treated for an additional 24 h with increasing concentrations of sulindac sulfide (0, 75,150, and 300 mM) (A) or sulindac sulfone (0, 300, 600, 1200 mmM) (B) in the absence of DFMO. Cells were replated at diluted concentrations and grown for 21 days. Plates were stained with crystal violet and the number of colonies on each plate was determined. Plating efficiency was determined by dividing the number of colonies by the total number of cells plated. These numbers were then normalized to the plating efficiency of non-drug-treated controls of the same line. Data points without error bars contain a standard deviation too small to be represented.
Figure 5B:
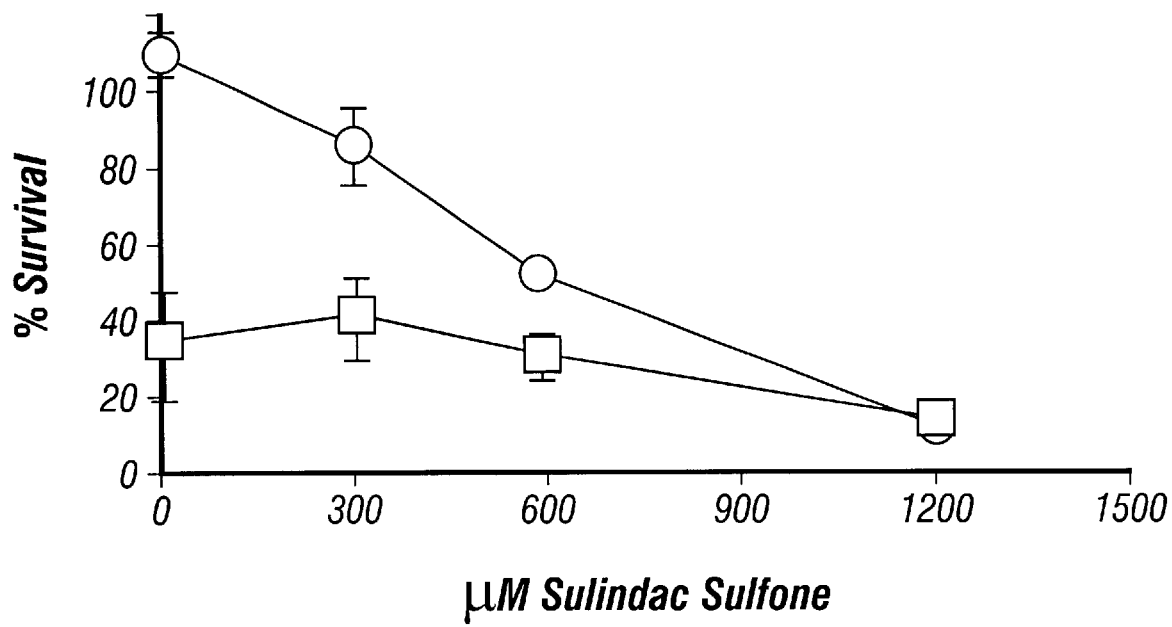

Effect of DFMO on the colony-forming efficiency of sulindac sulfone- and sulfide-treated Caco-2 cells Caco-2 cells and Ki-ras transfectants exhibit a growth cessation in response to polyamine depletion, which is not accompanied by a loss of viability in short-term experiments. Polyamine depletion in these experiments appears to have no effect on sulindac-induced cytotoxicity. To further characterize the effects of polyamine depletion, both alone and in combination with sulindac, colony forming efficiencies of Caco-2 and Clone 60 cells were analyzed after exposure to 5 mM DFMO and increasing concentrations of sulindac sulfide or sulfone (FIG. 5). Exposure of the Ki-ras transfected clones to 5 mM DFMO had a much more pronounced effect on cell survival than that exhibited by the parental Caco-2 cells. Treatment of the transfected cells with 5 mM DFMO alone resulted in a 60% decrease in cell survival compared to untreated transfectants, whereas in the parental cells, DFMO treatment alone had little effect. For both Caco-2 and clone 60 cell lines, the combination of DFMO and increasing concentrations of either sulindac metabolite resulted in an even further decrease in cell survival, which suggests that DFMO did not inhibit sulindac-induced cytotoxicity.

Figure 6A:
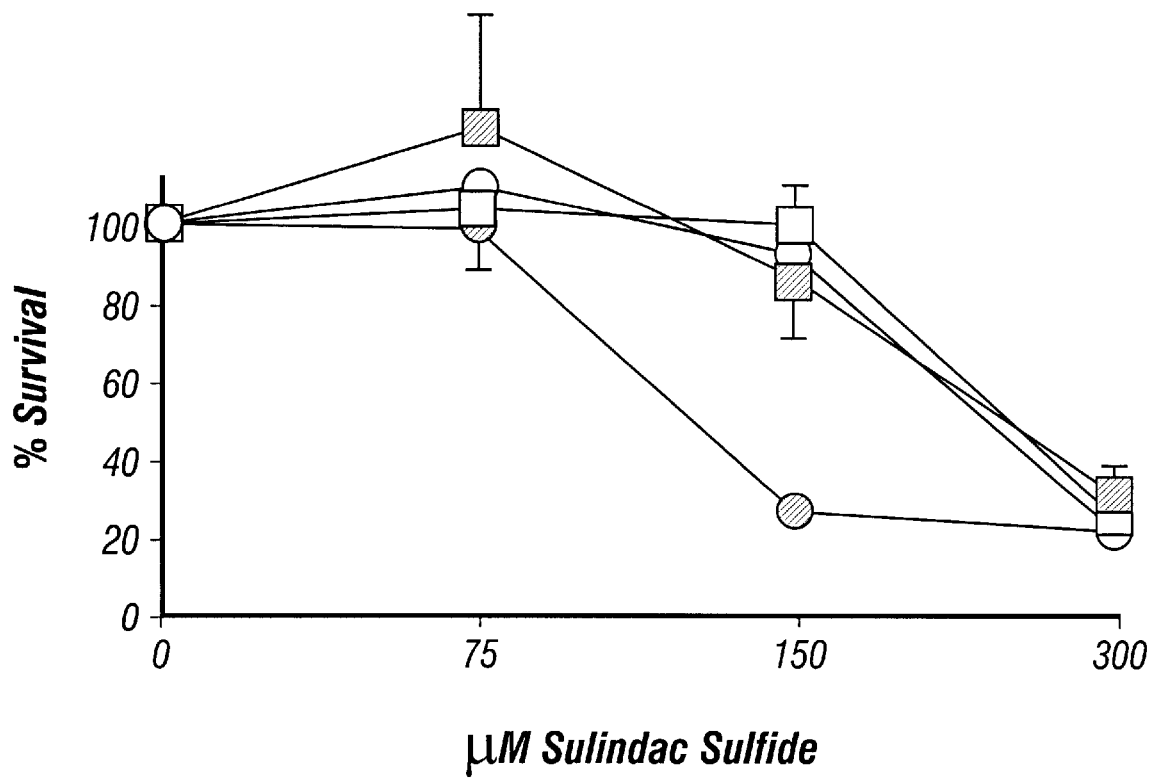
FIG. 6. Effect of DFMO on the dose-dependent toxicity of sulindac sulfide or sulfone. Caco-2 parental (○,●), or Ki-ras #60 cells (□,■) were treated with vehicle (○,□) or 5 mM difluoromethylomithine (DFMO) (●,■) for 24 h, and then treated for an additional 24 h with increasing concentrations of sulindac sulfide (0, 75, 150, and 300 μM) (A) or sulindac sulfone (0, 300, 600, and 1200 μM) (B), in the absence of DFMO. Cells were replated at diluted concentrations and grown for 21 days. Plates were stained with crystal violet and the number of colonies on each plate was determined. Plating efficiency was determined by dividing the number of colonies by the total number of cells plated. These values were then normalized to the plating efficiency of control cells that were treated similarly with respect to DFMO dosage. Data points without error bars contain a standard deviation too small to be represented.
Figure 6B:
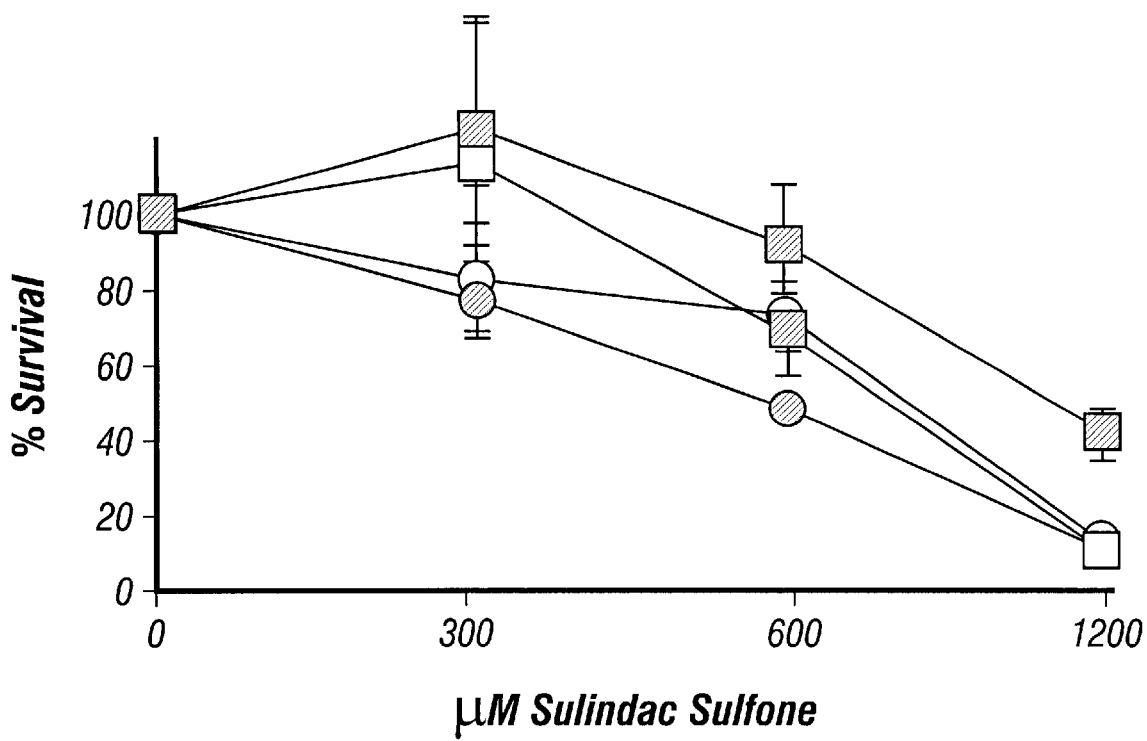

When the survival of DFMO-treated clone 60 or parental Caco-2 cells was normalized to like DFMO-treated controls, the survival rates of the DFMO-treated cells mirrored those of the non-DFMO-treated cells in response to increasing concentrations of sulindac sulfide (FIG. 6). Clone 60, which expressed an activated Ki-ras, was slightly more resistant to the effects of sulindac sulfone than the parental cells, regardless of whether or not DFMO was present.

Figure 7:
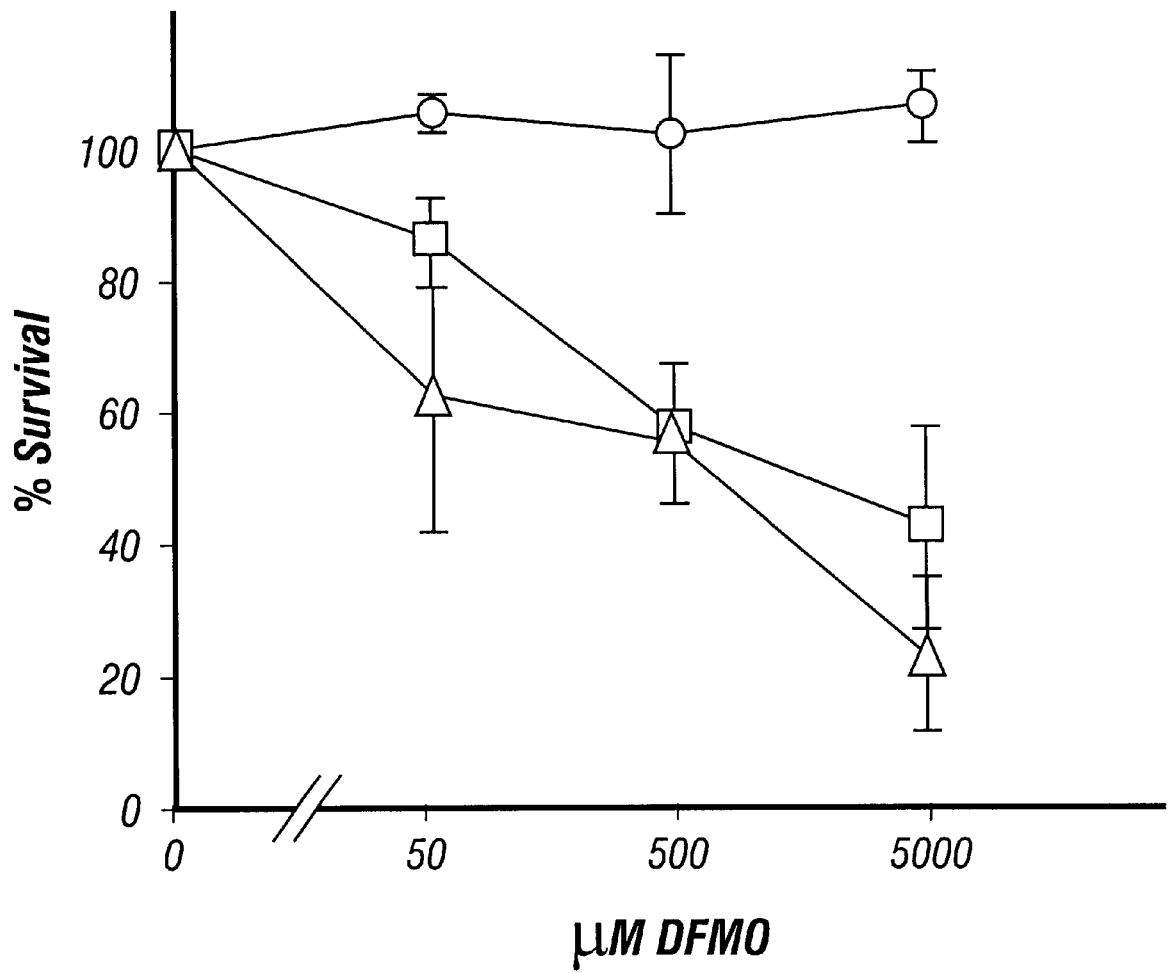
FIG. 7. Effect of DFMO on survival of Caco-2 and Ki-ras transfected cells. Caco-2 (●), Ki-ras #60 (■) or Ki-ras #66 (▲) cells were treated with 0, 50, 500, and 5000 μM DFMO for 24 h prior to subsequent dilution and reseeding in drug-free media Cells were grown for approximately 21 days and then analyzed for colony-forming efficiency. Plating efficiency was determined by dividing the number of colonies by the total number of cells plated. These values were then normalized to the plating efficiency of untreated control cells of like cell type. Data points without error bars contain a standard deviation too small to be represented.

Effect of increasing concentrations of DFMO on survival of cells with an activated Ki-ras The 60% decrease in survival of clone 60 clones treated with 5 mM DFMO suggests that polyamide was selectively toxic to cells expressing an activated Ki-ras. To further examine this response, Caco-2 cells and clones 60 and 66 were treated with increasing concentrations of DFMO for 24 hr and then replated for colony formation (FIG. 7). Caco-2 cells were refractory to DFMO treatment, and maintained nearly 100% survival at concentrations up to 5 mM DFMO. In contrast, both clone 60 and 66 exhibited increasing toxicity with increasing concentrations of DFMO, with 50% cell survival occurring at only 0.5 mM DFMO. At 5 mM DFMO, cell survival for both transfectants was decreased to 20–40% of controls. In these experiments, polyamine depletion was selectively toxic to cells with an activated Ki-ras at concentrations as low as 50 $\mu$M.

Figure 8A:
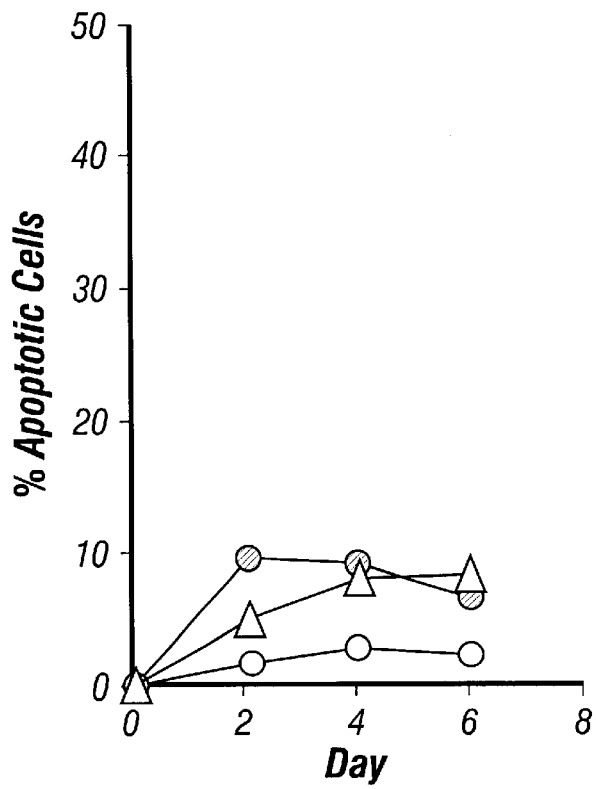
In FIG. 8A, -○-=Caco-2+DFMO, -Δ-= Caco-2+SN, and -●-=Caco-2+DFMO, SN.
Figure 8B:
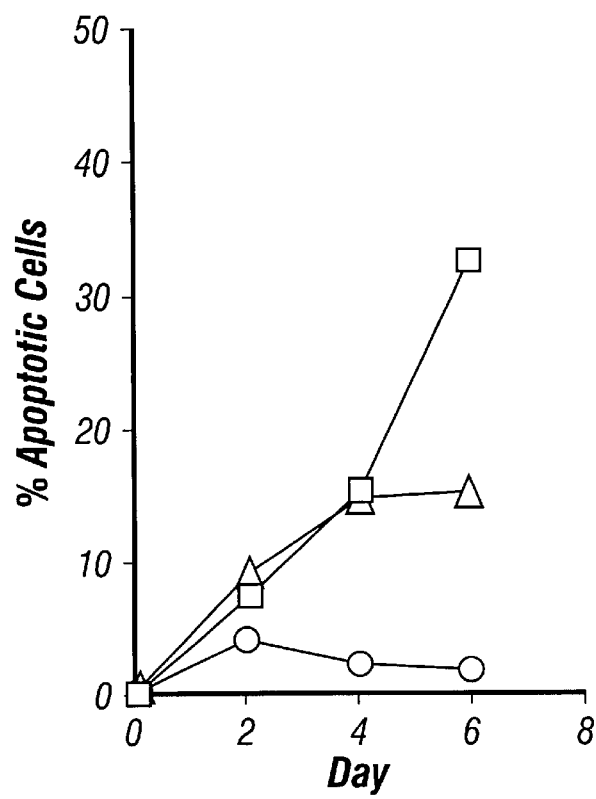
In FIG. 8B, -○-=#60+DFMO, -Δ-=#60+SN, and -■-=#60+DFMO, SN.

The effect of DFMO on apoptosis induced by sulfide or sulfone in Caco-2 parental or Ki-ras transfected cells Caco-2 cells or Caco-2 Ki-ras clone 60 were seeded in the presence or absence of 5 mM DFMO with or without 600 mM sulindac sulfone. Cells were grown over a period of 6 days. Cells were harvested at various days (0, 2, 4 and 6 days), spun onto slides and stained. Apoptosis was determined by light microscopy. Percentage of apoptotic cells was calculated as the number of apoptotic cells out of the total cells counted times 100. Results are shown in FIG. 8. Parental Caco-2 cells demonstrate only a modest increase in apoptosis upon treatment with DFMO or DFMO and sulindac sulfone (FIG. 8A). This is in contrast to the results of treating Caco-2 Ki-ras clone 60 with DFMO or DFMO and sulindac sulfone (FIG. 8B). DFMO alone increased apoptosis from low background levels of 2 to 4% to a high of 15% on day 6, while the combination DFMO and sulindac sulfone increased apoptosis to 33% on day 6 in clone 60.

Discusion

In the present study, the polyamine synthesis inhibitor α-difluoromethylornithine (DFMO) was selectively toxic to cells containing an activated Ki-ras. Ki-ras activation did not appear to render cells susceptible to cytotoxicity exerted by either metabolite of the NSAID sulindac. This suggests that the antitumor effects of DFMO and the NSAIDs seen in the AOM-rat model occur through different mechanisms.

The expression of an activated Ki-ras did not appear to change the growth rate of transfected cells, even in clones which expressed high levels of the protein nor did sulindac sulfide or sulfone exert a Ki-ras-specific effect on growth. This data is in contrast to work demonstrating a positive correlation between Ki-ras expression and growth rates in DLD-1 and HCT 116 human colon cell lines (Sharisawa et al., 1993).

A number of studies suggest that NSAID-mediated chemoprevention occurs through the induction of apoptosis (Bedi et al., 1995; Piazza et al., 1995; Boolbol et al., 1996; Samaha et al., 1997), however the role of Ki-ras activation in this process has not been extensively investigated. One group has found that Ki-ras activation in rat enterocytes confers resistance to apoptosis induced by sulindac sulfide although not with sulfone (Arber et al., 1997). In the present study, treatment of transfected Caco-2 cells with sulindac sulfide and sulfone resulted in a Ki-ras-dependent induction of apoptosis. Apoptosis induction by both sulfide and sulfone occurred several days earlier in Ki-ras transfected cells than in parental cells, although mammal levels of apoptosis in both transfectants and parental cells were similar. The efficacy of sulindac sulfone suggests the involvement of both prostaglandin-dependent and independent mechanisms.

The Ki-ras-dependent acceleration of apoptosis seen with sulindac treatment appeared to be inconsequential with respect to overall cytotoxicity. Survival studies with increasing concentrations of sulindac sulfide or sulfone did not reveal any differences in colony-forming efficiency between Ki-ras transfectants and parental Caco-2 cells, though cytotoxicity in both cell types was correlated with increased drug concentrations. This data suggests that although Ki-ras activation may render cells more susceptible to programmed cell death, the final level of cell survival influenced by sulindac metabolites occurred through a Ki-ras-independent mechanism.

The effect of the NSAIDs on Ki-ras mutation frequency of AOM-induced tumors also may be caused by a mechanism in which Ki-ras mutation is necessary but not sufficient to confer cytotoxic susceptibility. It is well-established that colon tumors arise as a result of multiple genetic alterations (Carethers, 1996; Vogelstein et al., 1988), a number of which are reproduced in the AOM-rat model of colon carcinogenesis (Erdman 1997; Singh and Reddy, 1995). Thus, the inhibition of tumorigenesis by sulindac may depend on the interaction of several altered signaling pathways, only one of which is influenced by an activated Ki-ras.

Administration of both piroxicam and DFMO in the AOM-rat model is synergistically chemopreventive, decreasing both the number of existing tumors as well as the number of tumors with an activated Ki-ras (Ready et al., 1990). In the present study, treatment of Caco-2 cells with DFMO did not increase the toxicity of the sulindac metabolites in long-term survival studies. Thus, DFMO and sulindac may utilize different mechanisms to prevent tumorigenesis.

This possibility is further supported by the selective cytotoxicity of DFMO seen in cells with an activated Ki-ras. Treatment of both Ki-ras clone 60 and 66 with increasing concentrations of DFMO led to a dose-dependent decrease in colony-forming efficiency, whereas survival of parental cells was unaffected. Twenty-four hours of treatment with 5 mM DFMO was sufficient to reduce colony-forming efficiency of the Ki-ras transfectants by 40%, even though cells were subsequently incubated in normal media for an additional 24 hours prior to replating. Concentrations as low as 50 μM DFMO were also moderately cytotoxic. In short-term growth studies, where cells were exposed to 5 mM DFMO continuously over a Sway time course, exclusion of trypan blue dye in either the Ki-ras cells or parentals was unaffected. The cells appeared to be metabolically active during this time period, yet the colony-forming efficiency data indicate they were unable to proliferate. The cytotoxicity of DFMO on cells with an activated Ki-ras is consistent with other studies showing potent chemopreventive effects of DFMO on AOM-induced tumorigenesis as well as the development of tumors with an activated Ki-ras (Singh et al., 1994; Kulkarni et al., 1992).

The mechanism by which DFMO prevents Ki-ras-dependent tumorigenesis in the AOM-rat model is unknown. It has been proposed that sulindac and DFMO act through a common pathway involving the inhibition of prostaglandin synthesis (Ready et al., 1990), since ODC activity can be inhibited by agents which inhibit cyclooxygenases (Reddy et al., 1990; Reddy et al., 1988). The induction of apoptosis may occur through the inhibition of prostaglandin synthesis, or in the case of sulindac sulfone, a prostaglandin-independent mechanism that is also independent of Ki-ras activation. The activation of Ki-ras may lead to the down-regulation of genes that are not necessary for growth, but are necessary for cell survival. This down regulation may not cause toxicity unless the cell undergoes the additional stress of polyamine depletion, in which case the genes normally expressed during conditions of stress are not available to protect the cell from a cytotoxic response.

EXAMPLE 2

The Min (multiple intestinal neoplasia) mouse, as a model of familial adenomatous polyposis (FAP), has provided important insights into the phenotype of the mutated APC/Apc gene (Lipkin, 1997). The Min mouse can develop greater than 100 gastrointestinal adenomas/adenocarcinomas throughout the gastrointestinal tract by 120 days of life leading to GI bleeding, obstruction and death. The present example demonstrates the utility of this model with respect to the present invention for treating and reducing gastrointestinal tumor development, and for identifying disturbances in polyamine metabolism as biochemical markers of altered growth and neoplasia.

Animal Model

Mice, purchased from The Jackson Laboratory (Bar Harbor, Me.), were bred crossing C57BL/6J-Apc$^{Min/+}$ males and C57/BL6 females. Heterozygous Min mice (Apc$^{Min}$/Apc$^+$): (heterozygous for a nonsense mutation at codon 850 of Apc) were identified by genotyping at weaning by an allele specific PCR™ assay using tail-tip DNA. Homozygous (Apc+/Apc+) litter mates served as controls. One treatment consisted of supplementing drinking water with 2% DFMO (Merrell Dow Research Inst.) on the 8th day of study. In the other treatment, 167 ppm of sulindac (Harlen Teklad) was added to AIN-93G mouse diet on the 21st day of the study. The third treatment was a combination of DFMO and sulindac.

Tissue collection

After 114 days, the mice were sacrificed through $CO_2$ asphyxiation. The small intestine and colon segments were removed from mice and dissected lengthwise, mounted and fixed in 70% ethanol, and placed at 4 degrees C for tumor scoring. Representative tissues were also taken for histopathology evaluation.

Proliferating Cell Nuclear Antigen

Ethanol fixed, paraffin-embedded sections of mouse small intestine and colon were evaluated by immunohistochemistry using a monoclonal anti-PCNA $PC_{10}$ antibody (Oncogene Science) was used. Standardized scoring methods were used to calculate a proliferative index based on an average of 15–20 villus-crypts (intestine) or crypt columns (colon) per sample.

Apoptosis Staining

Alterations in nuclear morphology (condensed chromatin, distinct apoptotic bodies) was the main endpoint used to score tissue in well oriented crypts and villi using standardized protocols to calculate the percent apoptotic cells per total counted.

Polyamine Assay

Polyamine (putresoine, spermidine, and spermine) levels were determined in acid-extracted samples by reverse-phase high performance liquid chromatography. The residual acid insoluble pellet was assayed for protein content by BCA (Pierce) with data expressed as nanomoles polyamine per mg protein.

Ornithine Decarboxylase (Odc) and Spermidine/spermnen$^1$-acetyltransferase ($N^1$ssat) Gene Expression Total RNA from whole intestine and colon was isolated using TRIzol reagent (Gibco, BRL). Northern blots were prepared and then hybridized with a $^{32}$P-labeled cDNA encoding for mouse ODC and for human $N^1$SSAT utilizing a random priming technique (Boehringer Mannheim). Data is expressed (relative gene expression) as the ratio of the integrated $^{32}$P-labeled hybridization band for the gene of interest and the integrated density of ethidium bromide stained 18S ribosome band.

Alterations in ODC gene expression and polyamine content are present in small intestinal and colonic tissues of Min mice when compared to litter mate controls. These findings are consistent with the disturbances of polyamine physiology that have been previously described in FAP patients (Luk et al., 1984; Giardiello et al., 1997). In the Min mouse model, tissue polyamine contents were elevated in the small intestines, but not the colon. The increased polyamine content in the small intestines was associated with an increase in ODC, and a decrease in antizyme, steady state RNA levels. These two changes would predict increased ODC-dependent polyamine contents in the small intestines of these mice.

Figure 9:
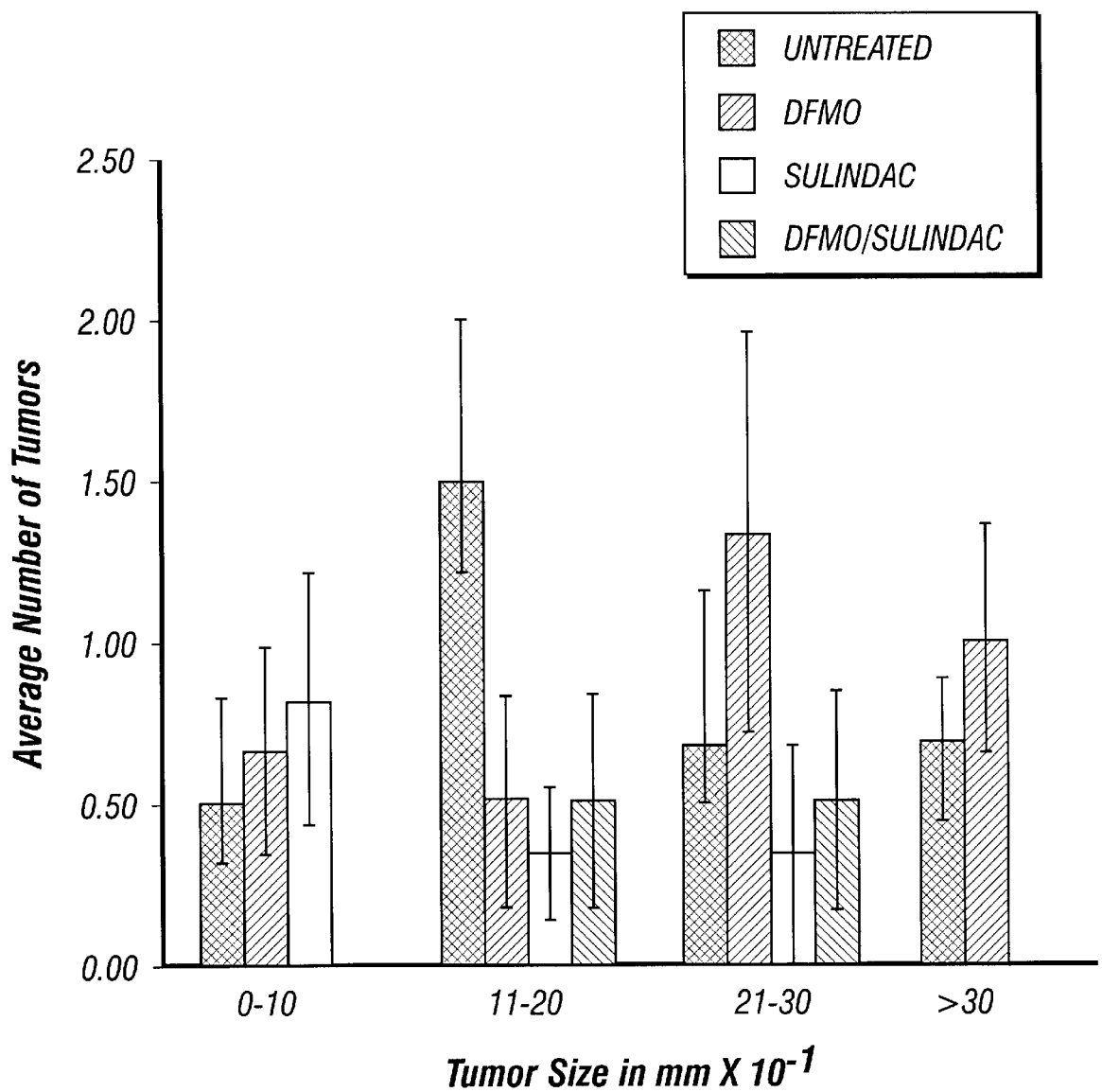
FIG. 9. Average number of tumors by size in the colon of Min mice treated with DFMO alone, sulindac alone and DFMO with sulindac as compared to untreated controls.
Figure 10:
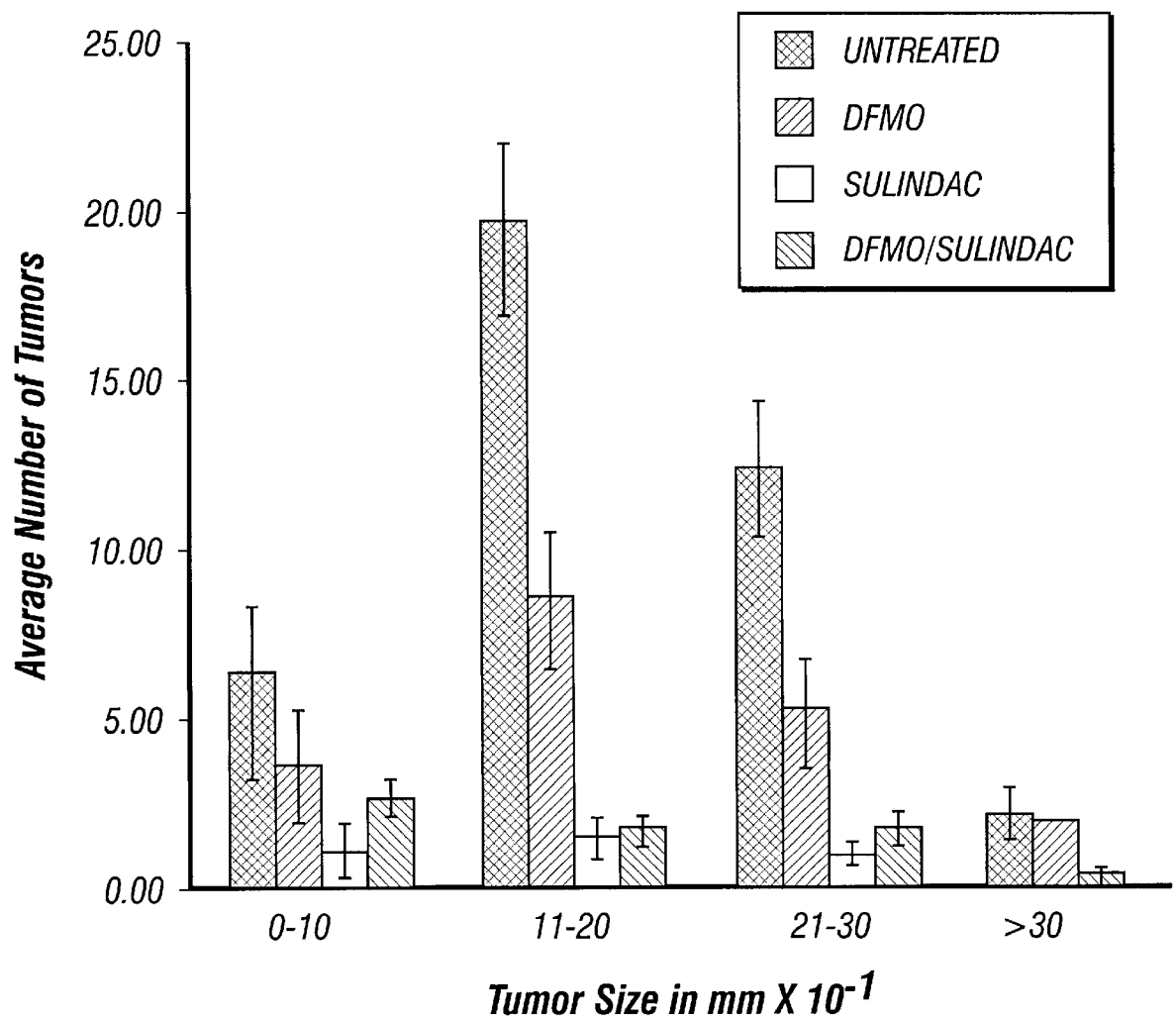
FIG. 10. Average number of tumors by size in the small intestine of Min mice treated with DFMO alone, sulindac alone and DFMO with sulindac as compared to untreated controls.

The results of treating Min mice with either DFMO alone, sulindac alone, or a combination of DFMO and sulindac on tumor formation in either the colon or small intestine are shown in FIG. 9 and FIG. 10. FIG. 9 shows the average number of tumors by size in the colon of the three treatment groups compared to untreated controls. FIG. 10 shows the average number of tumors by size in the small intestine of the three treatment groups compared to untreated controls.

EXAMPLE 3

Human Clinical Trials Studying the Effects of the Combination of DFMO and NSAID

I. Objectives

Colorectal cancer is a major national health problem for which there is not current preventative treatment other than expensive, inconvenient, and uncomfortable surveillance colonoscopy and polypectomy. Patients with adenomatous colon polyps are at increased risk of developing colon cancer. Epidemiologic studies suggest that non-steroidal anti-inflammatory agents (NSAIDs) protect against the development of colon cancer. Studies in animal models have demonstrated that carcinogen-induced colon cancer can be prevented, and that in particular, difluoromethylomithine (DFMO) and NSAIDs are efficacious. Several studies have now also shown that the NSAID sulindac can cause clinical regression of polyps. The inventors have considerable clinical experience with both these compounds and recently have completed clinical chemoprevention trials in subjects at increased risk for colon cancer: phase I (ibuprofen) and phase IIa (DFMO), phase IIb (DFMO, sulindac). Appropriate biochemical markers were measured in colonic mucosa and modulation demonstrated and regression of extant polyps shown (with Sulindac). In animals, combinations of agents acting through different mechanisms are more effective than either agent alone and the encouraging results (modulation of biochemical effect and no/low toxicity) in the clinical chemopreventive trials with these compounds suggests that a limited trial using a combination of these drugs is timely, feasible, and important. A randomized phase IIb clinical chemoprevention trial of the combination of DFMO and sulindac, both at low non-toxic doses, is described here.

The specific aims are:

(1) To measure the efficacy of DFMO plus Sulindac vs. placebo in modulating a panel of surrogate endpoint biomarkers (SEB) of particular relevance in colorectal neoplasia. Several measurements of quantitative histopathology and assessment of uninduced apoptosis, proliferative (Ki67) and preneoplastic (CEA, sialyl-TN, p53, bcl-2) features by immunoperoxidase will be done in biopsies of flat mucosa; polyamine and $PGE_2$ levels will also be determined as estimate of biochemical effect by the two agents.

(2) To determine the relationship between the modulation of SEB in flat mucosa to the development of interval incident adenomas, thereby validating the surrogate nature of one or more against adenoma pathology.

In these studies, biopsies of flat mucosal tissue (8–12 cm above the anal verge) will be sampled serially: (0 and 36 months, complete colonoscopy), (12 months, flexible sigmoidoscopy). New polyps will also be assessed for Ki-ras mutations and SEB. The participants will be carefully monitored by phone for potential side effects and adherence at 3 month intervals between yearly visits.

II. Treatment Plan

The dose of the drugs is: Sulindac 150 mg, orally, each day and DFMO 0.25/gm/day for three years.

III. Toxicities to be Monitored and Dose Modification

Five particular areas of concern have been identified with regard to the safety of subjects participating in this study and attempt to address each of them as outlined below. Given the low dose of the drugs, it is believed any acute side effect is almost non-existent, and there is relatively no risk of a major chronic side effect. Even at very high doses, all side effects hav e been reported to be completely reversible. The five main considerations are:

Thrombocytopenia (low platelet)

Thrombocytopenia has been reported predominantly in studies using "therapeutic" doses of DFMO (>g/m²/day) and primarily in cancer patients who had previously undergone chemotherapy or patients with compromised bone marrow.

Wound healing

DFMO may inhibit proliferative repair processes, such as epithelial wound healing. In DFMO studies employing administrations up to one year in duration—some of which included similar rectal biopsy procedures—those theoretical problems with wound healing have not been experienced. In the current protocol, which provides for extended dosing over a three-year period, this potential toxicity is monitored with vigilance. Second, the rectal biopsy procedure (sigmoidoscopy) performed during the study carries a very low risk of perforation of the rectum and of post-biopsy bleeding. No problems have been seen in the patients on the phase IIa trial nor have there been seen this side effect in ongoing phase I studies being conducted by other investigators. However, in those patients undergoing an occasional biopsy of the polyp greater than 1 cm the drugs are held for one week. Systemic infection from this breach of rectal mucosal integrity is also a remote possibility. Third, a colonoscopy is required for inclusion in and at completion of the study. This also carries the same risks as sigmoidoscopy plus an added risk of hemorrhage if polyps are found and removed by biopsy or electrocautery excision. It should be noted that the colonoscopies will be scheduled consistent with standard care for patients with prior polyps and do not represent an "extra" procedure.

Ulceration

Sulindac can cause G.I. ulceration that in general is dose-related. Its potential interaction with DFMO effect (i.e., possible delay in wound healing) is unknown. A significant portion of this problem may be due to the presence of *H. pylori* and therefore only patients that are antibody negative or who have undergone a course of antibiotics will be eligible for trial. Subjects are carefully monitored and have a CBC drawn every 6 months to detect occult blood loss.

Hearing loss

Hearing loss may occur in association with DFMO administration at high doses. In a previous study (Croghan et al., 1991), it was reported that less than 10% of the patients who received cumulative doses below 150 g/m² developed a demonstrable hearing deficit, while hearing losses were observed in up to 75% of patients who received cumulative doses above 250 g/m². This side effect has been totally reversible upon drug discontinuation. In two phase I trials done by other investigators, no audiometric changes were seen after about 6 months of DFMO at 0.50 g/m²/d (total dose 90 gm) although changes were seen at higher doses. Additionally, with DFMO at the highest dose group (0.4 gm/m 2/day), which represents a total dose of 144 mg/m² no detectable audiologic change was observed. At low doses of DFMO, ongoing recovery of inner ear polyamines may occur and hearing loss will be rare. The dose chosen for the trial is 0.25 g/m²/d. If hearing loss is detected, it should not occur until after 800 days.

Venous access

Blood specimens are obtained from an arm vein, carrying the risk of bruising and local infection.

Sulindac Specific Adverse Events

Sulindac is a nonsteroidal anti-inflammatory analgesic (NSAID). The study dosage used is 150 mg by mouth once a day, half the normal starting therapeutic dosage. As with other NSAIDs, Sulindac can produce gastric irritation and bleeding. At therapeutic doses and in order of frequency, adverse effects reported were gastrointestinal pain (10%); dyspepsia, diarrhea, nausea, constipation (3%–9%), and flatulence, cramping, anorexia (1%–3%).

Gastrointestinal bleeding is reported with NSAIDs in general, and include ulcerations, bleeding and perforation, 1% of patients treated after 3 to 6 months and 2%–4% after one year will develop ulcers, bleeding or perforation. Previous ulceration is the most predictive risk factor.

Other systems with adverse effects in the 3%–9% range are skin rash, dizziness and headache.

Adverse effects reported in 1%–3% of cases are fluid retention and edema, nervousness, pruritus, and tinnitus. Rare adverse effects less than 1% include granulocytosis, aplastic anemia, hemolytic anemia. Sulindac may inhibit platelet aggregation and prolong bleeding time. These effects are of short duration and resolve after the drug leaves the system (half-life of 7 hr). Hypertension and congestive heart failure is rare, as is hyperkalemia, hyperthermia, pancreatitis (elevation in serum lipase and amylase). Borderline elevations in one or more liver function test have been reported in 15% of clinical trial patients, but meaningful elevations (3 times upper limit of normal) have occurred in less than 1%. Gouty arthritis may be masked by NSAIDs.

DFMO Specific Adverse Events

DFMO has in other clinical trials shown to have effects on hearing that resolve when it is discontinued, however this was not demonstrated in the recent phase IIB trial with doses up to 0.4 mg/m² for one year. Tinnitus was al so tracked as a finding. In addition a few cases of dizziness/vertigo that resolved when the drug was stopped were noted. These participants will be taking low doses of DFMO and Sulindac and are monitored closely for any possible additive effect in these two areas.

Measures to Minimize Risk and Ensure Subject Safety

Baseline urine and blood tests done (chemistry panel, CBC) includes liver function tests, amylase, lipase, BUN, creatinine, and complete blood counts and repeat as needed.

IV. Background

Extensive literature, including epidemiologic and animal model studies, suggests that NSMDs can reduce the appearance of colon polyps and cancer. Extensive studies in animal models substantiate that the polyamine synthesis inhibitor DFMO inhibits the development of many cancers including carcinogen-induced colon polyps and cancer.

Key elements affecting design of the trial are reviewed here.

(1) Choice and dose of agents.

When choosing the dose of an agent that will be used in a combination it should be assumed that toxicity of the two compounds may be synergistic. This is particularly important in trials that involve relatively healthy people and mandates that as low a dose as possible (ie. the lowest dose that demonstrates consistent biochemical effect in the relevant tissue ) be used.

(a) NSAID—Sulindac

Chemoprevention studies of Ibuprofen, Piroxicam, and Sulindac against colon carcinogenesis have been reported in animal models (Moorghen et al., 1988; Pollard at al., 1989; Reddy et al., 1987). The major mechanisms by which this effect are mediated is not clearly defined but interactions with the cell cycle and apoptotic responses are likely (Pasricha et al., 1995; Piazza et al., 1995; Shiff et al., 1996; Shiff et al., 1995). The inventors have recently completed a phase Ia trial (one month) of Ibuprofen and even at the dose of 300 mg/day a significant decrease in $PGE_2$ levels in flat mucosa was seen. A dose of 300 mg of Ibuprofen is very low (therapeutic doses range from 1200–3000 mg/day or more)

and toxicity is unlikely to be seen, even over the long-term. However in animal chemoprevention models Ibuprofen is less effective than other NSAIDs. Although Piroxicam is the most effective chemoprevention agent in animal models (Pollard et al., 1989; Reddy et al., 1987), it demonstrated side effects in the recent IIb trial. A large meta-analysis of the side effects of the NSAIDs also indicates that piroxicam has more side effects than other NSAIDs (Lanza et al., 1995). Sulindac has been shown to produce regression of adenomas in FAP patients (Muscat et al., 1994). Although at least one study in sporadic adenomas has shown no such effect (Ladenheim et al., 1995), the inventors have recently completed a randomized phase IIb study that shows that Sulindac is safe and that this compound may cause polyp regression and inhibit the development of new polyps as well (DiSario et al., 1997). Although the study was relatively small, a dose of 150 mg per day vs. twice per day appeared to produce comparable results. Although arguments can be made pro and con for the choice of NSAIDs, the assessment suggests that the efficacy of Sulindac in causing regression of human adenomas and its favorable safety/toxicity favors its use in combination trials compared to other NSAIDs. The inventors have therefore selected Sulindac at a dose of 150 mg per day as the NSAID to be used in the current example.

(b) DFMO

The inventors have recently reported the results of a phase IIa (one month) dose de-escalation trial of DFMO and effects on polyamine metabolism were evident at a dose as low as 0.2 $Gm/M^2/day$ and perhaps even lower (Meyskens et al., 1994). The inventors have finished a longer term trial (12 months) and have final 12 month results for all participants. These results indicate that even a dose as low as 0.10 $Gm/M^2/day$ may produce a persistent effect on polyamine levels. After one year the side-effects of all dosage groups were equivalent to placebo and no audiotoxicity was evident. There was, however, a suggestion that patients on the highest dose (0.40 $Gm/M^2/day$) came off study more frequently due tot he cumulative influence of a constellation of mild symptoms. Based on this information a dose of 0.2 $Gm/M^2/day$ will be used for the current trial.

The effect of DFMO and Sulindac on modulating the relevant biochemical effect in the target organ of interest (flat colonic mucosa) is determined by serial measurements respectively of polyamines (putrescine levels and Spd/Spm ratio) and $PGE_2$ levels.

(2) Pre-Eligibility Considerations

A major issue is whether potential participants in this trial who are receiving aspirin for cardiovascular disease prophylaxis should be allowed to enter the trial. Concern exists at two levels: (a) potential additive toxicity; (b) confounding of the potential chemopreventive effect. The dose of aspirin used for prophylaxis is 81 mg per day ("baby aspirin") and unfavorable effects are near to none. Although many of the observational studies have suggested a beneficial effect of aspirin on colon cancer incidence, such effects probably become evident only at a weekly total dose of 1000 mg or greater (Giovannucci et al., 1994). Additionally, three large cohort studies have produced conflicting reports on the beneficial effect of aspirin (Gann et al., Giovannucci et al., 1994; Greenberg et al., 1993). However, one group of inventors have recently shown that $PGF_{2\alpha}$ is decreased in colon mucosa by a dose as low as 40 mg and that $PGE_2$ can be decreased at a dose between 80 and 160 mg/day. In contrast another group of investigators have shown no such effect on colon mucosal prostaglandins at these low doses of aspirin, although substantial reduction of prostaglandins in upper gastrointestinal mucosa was demonstrated. The inventors interpret the results of these studies to indicate that a dose of aspirin of 81 mg is at the threshold of effect of this agent on colon mucosa.

In addition, there is the practical consideration that more and more individuals are going on low-dose prophylactic aspirin and that for any trial to be generalizable this fact needs to be acknowledged. After considerable discussion the investigators have unanimously agreed to allow entry into study of individuals who are taking no more than one "baby aspirin" per day.

(3) *H. pylori* Prophylaxis

A considerable amount of data indicates that *H. pylori* positivity may contribute significantly to NSAID toxicity. The risk of developing peptic ulcer disease increases with use of long-term, high dose NSAIDs to 3 to 4 times that of non-users. A preexisting *H. pylori* infection increases the risk of gastric ulcer 3 to 4 fold. To reduce possible risk to participants who are randomized to low-dose sulindac and DFMO, a serum antibody screen will be obtained. Those who are positive will undergo a 2 week prophylactic course of "triple therapy" before randomization. Once the participant has completed the prophylactic course of "triple therapy" they are eligible for study randomization.

A preferred regimen at this time includes omeprazole 20 mg by mouth twice a day, metronidazole 250 mg or 500 mg by mouth four times a day, and clarithrymycin 250 mg or 500 mg by mouth three times a day (regimen referred to as MOC). At this time a fourteen day course is recommended, however, studies have shown that a seven day course is as effective in eradicating the infection. Adverse effects possible from this triple therapy are dizziness (2%) with omeprazole; metallic taste, vomiting, anorexia, headache, fever, rash (5%), neuropathy, and disulfiram-like reaction with alcohol ingestion (20%) with metronidazole. Clarithromycin may cause diarrhea (10%) nausea, dyspepsia, headache, and rarely, pseudomembranous colitis (1%). All participants who are on this regimen prior to enrollment are monitored closely for any adverse reactions.

Another favored triple treatment regimen includes twice daily doses of lansoprazole, 30 mg, amoxicillin 1 gm, and clarithromycin 500 mg. This easy to follow dosing regimen is recommended to be 10 to 14 days in length for optimal treatment of *H pylori*. Possible adverse effects are: with lansoprazole—headache (5%), diarrhea (8%), nausea (3%); with amoxicillin—diarrhea and super-infections; and with clarithromycin—diarrhea (10%), nausea, dyspepsia, headache, and rarely, pseudomembranous colitis (1%). Participants are solicited for comments regarding possible side effects while on this prophylactic regimen.

(4) Potential Surrogate Endpoint Biomarkers (SEB)

The number of markers that could be selected is long and investigators have their favorites. It is important to recognize that no SEB to date has been shown to be a surrogate for cancer; i.e., the inventors do not yet have the equivalent of cholesterol and cardiovascular disease for cancer and the selection needs to be influenced by: relevance, cost and feasibility. In the current contract the inventors measure:

morphometric—image analysis of nuclear morphometry and texture, and ploidy.

assessment of proliferative (Ki67) and preneoplastic (CEA, Sialyl-TN, p53, bcl-2) features by immunoperoxidase staining.

measurement of uninduced apoptosis.

(5) Polymanagement and recurrence.

There have been a large number of studies documenting the recurrence of polyps after colonoscopy and polypectomy. There is a general consensus that follow-up every three years by colonoscopy is appropriate and the recurrence rate of incident adenomatous polyps will be about 30–35% during this time period. Patients also undergo flexible sigmoidoscopy after 12 months of therapy at which time biopsies for SEB and polyamine and prostaglandin levels will be obtain.

(6) Number of participants and length of trial.

The inventors are studying 250 participants entered into a placebo-controlled, randomized, two-arm study, who are followed for three years. It is anticipated that 200 will complete the course. Full colonoscopies are done at time zero and after 36 months (or earlier if relevant symptomatology develops) and all polyps will be removed. Eight flat mucosal biopsies will be obtained at 8–12 cm above the anal verge at these time points and after 12 months on therapy (7) Monitoring of Stool OB Because the colon is under greater than standard surveillance and subjects may receive a potential chemopreventive agent as well, occult blood monitoring as a means to bolster human safety may not be efficacious. It is likely to be associated with a very high rate of false-positivity and therefore offer little—or more likely—no benefit to the subjects, while potentially damaging the quality of the study by effectively unmasking treatment allocations and/or adding to temporal variation in the endoscopic assessments (if a substantial number are required to be done off-schedule for hemoccult positive results).

(8) Many of the patients will have primary care physicians who would follow the ACS recommendations of a yearly stool OB in individuals over age 50. Since all participants will have had a clear colonsocopy at study entry, the inventors are asking all primary care physicians not to obtain a routine screening OB during the time the patient is on study unless such is clinically indicated. Nevertheless as a safety measure, all patients will have a CBC at 3/6 months on study medication and at 6 month intervals thereafter. If a fall in hemoglobin of grater than 10% is noted, appropriate medical follow-up will occur.

V. Methods

Laboratory Assays

Eight biopsies of the flat mucosa are taken 8–12 cm above the anal verge. Five specimens are snap-frozen in liquid nitrogen and stored in a −80 freezer until use. Three specimens are fixed in formalin. Any polyps that are removed undergo routine histopathological analysis and fixation in formalin for p53 or K-ras analysis.

Measurement of polyamine endpoints in human colorectal normal and neoplastic tissues.

The objective of this component is to measure parameters of polyamine metabolism in tissues and document the efficacy of α-diflouromethylornithine (DFMO) on this metabolism. Other groups have reported elevations in ODC activity in precancers in epithelial tissues, but there is controversy in the literature on this point (Porter et al., 1987; Braverman et al., 1990). Since a number of factors, the inventors set out to systematically evaluate errors associated with these measurements in human tissue biopsies. Because one of the interests is the chemoprevention of colorectal cancer, and since the colorectal tissue is accessible for collection, the inventors choose colon/rectum as the site for these studies.

Pathology—Specimen Handling and Processing

At each colonoscopy or sigmoidoscopy procedure, two formalin-fixed biopsies of normal colon and any polyps embedded in paraffin, are analyzed. Paraffin embedded tissue is primarily used for this study because of its several advantages. First, the tissue can be assessed morphologically for dysplasia, hyperplasia, inflammation or invasive carcinoma. Second, many of the immunohistochemical markers for proliferation and pre-malignant change are available for paraffin embedded tissue. Third, the tissue is suitable for use in morphometric studies and finally, paraffin blocks can be stored for prolonged periods without loss of antigenicity or DNA degradation. And fourth, the tissue is safely and easily transportable in this form.

Immunoperoxidase

After morphological assessment on hematoxylin and eosin stains, sections are stained for markers for proliferation and pre-malignancy. the best of the former is MIB-47 1, which is reactive with a formalin-resistant epitope of KI-67. Expression of this marker shows a high correlation with S-phase fraction by flow cytometry (Keshgegian and Cnaan, 1995). Proliferation is determined from the percentage of 500 cells displaying nuclear immunoreactivity. Two useful pre-neoplastic markers are CEA and sialyl-Tn (Xu et al., 1989). Immunoreactivity is estimated by grading mucosal cells as negative, weakly positive, or strongly positive, or by optical density equantitation using the CAS system. The percentage of cells is determined for each staining category. Additional preneoplastic markers can be added to this panel as they become available (i.e., Bcl-2, NM (Liao et al., 1994), CMU 10 (Yang and Shamsuddin, 1995). Finally, p53 is assessed using the D07 antibody, which detects both native and mutant p53 (Voytesek et al., 1992). Although p53 mutation is considered a relatively late feature of colon carcinogenesis, a quantitative assessment of p53 staining nuclei (% p53 positive nuclei in 500 cells) may detect subtle early lesions in the mucosa. The main disadvantage of p53 assessment using immunoperoxidase is that if only a few cells are positive, whether they are mutated or wild-type p53 cannot be easily determined.

Image Analysis

The paraffin embedded tissue is also be used for morphometry. Nuclei in mucosal crypts and adenomas can overlap substantially, which makes image analysis from cut sections inaccurate. Therefore, 50 $\mu$m sections are microdissected to remove stroma and disaggregated using a procedure supplied by Becton Dicksinson. Briefly sections are deparaffinized, rehydrated, pepsin treated, cytocentrifuged and Feulgen stained. These preparations are used for both ploidy and analysis and nuclear measurements. The major disadvantage of this approach is that stromal cells and epithelial cells are not always readily distinguishable in these preparations. If necessary, sections are stained with anti-keratin antibodies by immunoperoxidase to confirm that the nuclei analyzed are epithelial in origin.

The methods for image analysis optimized for the CAS 200 Image Processing System (Becton Dickinson, San Jose, Calif.) are well characterized and have been described in the literature (Bacus and Bacus, 1994; Bacus and Grace, 1987). Briefly, approximately 200–500 Feulgen-stained nuclei displayed on the computer screen are automatically chosen by the computer. Operator intervention may be necessary to pick optimum nuclei. The computer calculates the optical density (OD) per nucleus, which is proportional to the DNA content. From this measure a histogram of the percentage of cells at each OD can be constructed. The peak indicates the ploidy, which is compared to a standard diploid cell population such as rat hepatocyte nuclei.

Using the cell Morphology Program of the CAS 200, additional measurements, such as nuclear area, shape and texture is obtained. Area is determined from the total number of pixels per nucleus and shape is computed from a combination of perimeter measurements and object size. The texture is determined by computing the standard deviation of OD over all the individual pixels in the nucleus. In addition, Markovian texture measurements can be calculated by comparing a pixel OD to the ODs of the nearest neighbors. Twenty-two Markovian texture calculations are available on the software of the CAS 200 system (Bacus and Grace, 1987).

Determination of nucleolar size also takes advantage of the micrometer function of the CAS 200 system. In Feulgein-stained preparations, the nucleoli do not stain, but are surrounded by chromatin and appear as a hole. The radius of this circle can be determined and averaged over all the nuclei in the chosen sample. Similarly, the average number of nucleoli per cell can be determined by counting the total number of nucleoli in the nuclear sample and dividing by the total number of nuclei in the sample.

DNA extraction from paraffin embedded tissues.

Two to three 10–25 mm microtome slices are produced from paraffin embedded tumor samples, and DNA is extracted from paraffin embedded tumors or frozen samples. The proteinase K tissues are digested overnight and then extracted with three, equal volume phenol/chloroform (Tris-equilibrated, pH 8.0) washes. An additional chloroform wash is used to remove any excess phenol. The aqueous phase containing the DNA will be pelted at 12,000×g for 5" at room temperature and washed twice with 75% ethanol. Pelted DNA is briefly dried in a Speed-Vac (Savant) and resolubilized in autoclaved, filtered water overnight for use in polymerase chain reaction (PCR™). PCR™-RFLP.

A PCR™-RFLP assay is used to screen for codon 12 mutations in Ki-ras in colon adenocarcinomas from AOM-treated rats, because more than 60% of Ki-ras mutations in these tumors occur at this site (Jiang et al., 1989). PCR™ will be performed using primers designed to create a BstN1 restriction endonuclease site at codon 12 of the Ki-ras gene as described (Searle et al., 1982) a G→C change made at codon 11.3 bp from the 3' end of the wildtype upstream primer: 5'AAACTTGTGGAGTTGGACCT-3') Ki-ras mutations are determined by whether a change had occurred in the BsN1 site. If a mutation had occurred, no change in base pair length from uncut PCR™ fragments would occur. Restriction enzyme digested PCR™ products were electrophoresed on a 3.5% agarose gel, stained with ethidium bromide, and visualized under 300 fnm UV trans-illumination for the presence of mutations.

Putative Ki-ras mutations detected by this assay method in colon adenocarcinomas obtained from AOM-treated rats will be confirmed by DNA sequencing methods.

PGE2 Measurement.

Rectal mucosal biopsies are placed in a cryovial containing 5 mg/ml indomethacin which instantaneously and reliably halts in vitro PGE2 synthesis, snap frozen in liquid nitrogen and stored in liquid nitrogen until time of assay. At time of assay, the biopsy is thawed and placed in a siliconized 5.0 ml glass/glass tissue grinder in 1.0 ml of 0.05 M Tris-HCI, pH 7.4 containing 5 mg/ml indomethacin. Tissue is homogenized for 30 sec and 100 microliters are removed for protein determinations. One hundred percent ethanol (ETOH) (2.0 ml) is added to the remaining homogenated, vortexed and allowed to stand for 5 min on ice. Distilled water (10.3 ml) is added to the homogenate (final concentration, 15% EtEOHO and the sample is centrifuged 10 min at 400×g at 4 degrees C. The supernatant is removed and the pH is adjusted to 3.0 with 0.25 M HCI. the sample is then applied to a C18 silica column previously washed with 20 ml 100% EtOH followed by 20 ml distilled water. The column is rinsed with 20 ml of a 15% EtOH solution followed by 20 ml petroleum ether. PGE2 is gravity-eluted with 10 ml methyl formate. The methyl formate is divided into 4 equal 2.5 ml aliquots, dried under nitrogen, and stored at −80 degrees C. Samples are reconstituted in 0.25 ml assay buffer and as sayed for PGE2 content using a Dupont $^{125}$I-PE$_2$RIA kit.

Quality Assurance (QA)/Quality Control (QC)

Multiple colorectal biopsies were obtained from 39 patients undergoing colonoscopy. Biopsy size affected polyamine, but not ODC values. Spermidine (spd); spermine (spm) ratios are varied less than the contents of the individual amines. Bowel preparation methods did not affect any of the measurements. ODC activities and spd:spm ratios did not vary with bowel location. Lab assay methods contributed to sources of error. Variability was greatest for polyamine content measurements, but was reduced when polyamine contents were analyzed as spd:spm ratios. Intrapatient variability of these parameters was great or greater than interpatient variability. When measured in apparently unaffected colorectal mucosa, none of these parameters were significantly correlated with prior polyp history, prevalent polyps found at current colonscopy or polyp size.

Using this information regarding sources of error, the inventors also measured ODC activity and polyamine contents in tissue samples obtained during colonoscopy from 48 benign neoplastic polyps (20 tubular adenomas, 28 villous adenomas), 18 cancers (including 5 malignant polyps) and adjacent mucosa. ODC activity in polyp and cancer tissue specimens was higher than in adjacent mucosa in 75 and 83% of pairs, respectively. Similarly, putrescine, spermidine and spermine contents and polyamine content in colonic mucosa from 10 patients without a history of colorectal neoplasia were not different from adjacent mucosal values in the patients with neoplasia. From these measurements, the inventors concluded that ODC and polyamine contents are elevated in majority of colorectal neoplasia, but amounts in normal mucosa do not differentiate between patients with cancer, benign neoplastic polyps and normal subjects. Thus neither ODC activity nor polyamine contents of normal mucosa appear to be discriminatory markers of colorectal carcinogenesis. However, spd:spm rations, which show the least variability among measures of polyamine contents, were a good marker of the consequence of polyamine synthesis inhibition in chemoprevention trials. Details regarding the results summarized in this section have been published (Hixson et al., 1993; Hixson et al., 1994; Einspahr et al., 1995).

VI. Results

Effects in Tissues

When the inventors started these studies, their hope was that the effects of polyamine syntheses inhibitors in easily accessible tissues, such as buccal mucosa in the oral cavity, would be representative of inhibitor effects in less accessible tissue of the gastrointestinal tract. To test this hypothesis, the inventors measured ODC activity and polyamine contents in buccal mucosa isolated from normal human volunteers. The inventors found that the majority of ODC activity in buccal mucosa was due to oral bacteria that was not separable from the human cells by extensive washing procedures. While DFMO reduced polyamine contents in colorectal tissue biopsies, buccal mucosal ODC and polyamine contents were unaffected. From these studies, the inventors concluded that the buccal mucosal was not a useful surrogate tissue in which to measure the effects of polyamine synthesis inhibitor on other GI tissues.

The inventors then investigated the effects of DFMO on gastrointestinal tissue polyamine contents in two patient populations. One group included patients with Barrett's esophagus, a precancer associated with an elevated risk of the development of denocarcinoma of the esophagus. The other group included patients with recurrent olon polyps. A precancer associated with an elevated risk of developing colon cancer.

In the Barrett's esophagus group, patients were treated with DFMO 1.5 gm/m$^2$ per day) for 12 weeks. Four sites (Barrett's lesion, adjacent normal squamous esophagus, gastric tissue and small bowel) were biopsied in each patient before during and after DFMO treatment in order to assess the effects of this drug on tissue polyamine levels. ODC activities and polyamine contents varied in each site analyzed. The rank orders were Barrett's>small bowel~normal esophagus>gastric tissue for ODC activities, and small bowel≧Barrett's~normal esophagus>gastric tissue for putrescine contents. Spermidine, but not spermine, contents in Barrett's lesions and normal squamous esophageal tissue were suppressed by systemic DFMO treatment and recovered to untreated control values when DFMO therapy was discontinued. Systemic DFMO treatment did not affect the levels of either of these two amines in gastric tissue and small bowel. Since DFMO can suppress polyamine contents in several human gastrointestinal tissues, including Barrett's mucosa, the inventors concluded that DFMO would be an effective agent to test the hypothesis that depletion of spermidine contents may prevent the development of adenocarcinoma of the specific patient group.

In the group, 111 patients, who had undergone colonscopy for surgical removal of an adenomatous colon polyp greater than 5 mm within 5 years prior to enter the study, were treated with DFMO for 4 wk to determine the lowest does of this agent which would suppress colorectal tissue polyamine contents. A dose de-escalation trial design was employed, in which groups of patients (12–20 patients per group) were treated with single daily doses of DFMO ranging from 3.0 to 0.1 gm/m$^2$. Prior to initiation of DFMO treatment and at the end of treatment, six colorectal biopsy specimens were collected from patient along with serum samples. All biopsies were performed between 9:00 a.m. and noon to avoid possible effects of diurnal variation in laboratory endpoints. Samples for analysis of plasma DFMO levels were also collected during this time period of the day after the last day of drug administration. DFMO caused a decrease in both putrescine content and the ration of spd:smp for all dose groups down to 0.25 gm/m$^2$. Both putrescine content and the spd:smp ratio, and changes in these parameters as a function of DFMO treatment, decreased as function of donor age. None of the 30 patients receiving either 0.25 or 0.5 gm/m$^2$ experienced any clinical ototoxicity in this trial. The inventors concluded that DFMO was both safe and effective in reducing colorectal mucosal polyamine contents when administered daily orally to patients at doses as low as 0.25 gm/m$^2$ for 28 days. No ototoxicity was observed at doses up to twice this amount. Details of this work have been published (Meyskens et al., 1994; Boyle et al., 1992; Gerner et al., 1994; Meyskens et al., 1992; Meyskens et al., 1995).

Measurement of cell death, including apoptosis.

Apoptosis and necrosis are two distinct modes of cell death (Walker et al., 1988; Searle et al., 1982; Wyllie, 1981; Kerr et al., 1972; Kerr et al., 1987). Apoptosis is a controlled mode of cell death in which the dying cell takes an active role in its own demise. Classical necrosis, however, is a traumatic or accidental mode of cell death resulting, for example, from extremes in environmental conditions. John Kerr first recognized apoptosis as a distinct mode of cell death in 1972, and described this process at the ultrastructural level (Kerr et al., 1972). The sub-cellular features that characterize apoptotic cells include a condensation and margination of the chromatin, increased electron density, cytoplasmic vacuolization, fragmentation of the nucleus into membrane-bound bodies, and apoptotic body formation (Kerr et al., 1972; Payne et al., 1992). Time-lapse cinematographic studies indicate the dramatic surface changes that accompany apoptosis ("cell boiling" and shrinkage) and the explosive nature (cell swelling and membrane rupture) of a cell undergoing necrosis (Matter, 1979; Russell et al., 1972; Sanderson, 1981).

Since these early ultrastructural studies, many light (Payne et al., 1995) and biochemical assays have been utilized to identify apoptotic cells to replace the time-consuming ultrastructural evaluations. The inventors are using bright field microscopic methods as the main technique for assessing apoptosis in the proposed studies.

Apoptosis in uninduced tissue is measured in apparently normal colonic mucosa and in colon polyps. Preliminary studies in the inventors' group to date, in both experimental animal models (rodents) and humans, indicate that the baseline values of apoptosis in apparently normal colonic mucosa are heterogeneous (generally apoptotic cells are found at the top of the crypt, less frequently at the base) and low (less than 4%).

The tissue is fixed in formalin and three micron sections are then prepared using glass knives, stained with Methylene Blue/Azure II/Basic Fuchsin (a polychrome stain) and the number of cells with "darkly-stained" (apoptotic) and "lightly-stained" (non-apoptotic) nuclei is determined by light microscopy.

All cells in the crypts are stored in this assay. The criteria used to identify apoptotic cells are based on the increased staining intensity of the nuclei and is determined from at least 10 different crypts per biopsy. A minimum of 200 cells is scored per biopsy. The identification of apoptotic cells by light microscopy has been confirmed by electron microscopy (Samaha et al., 1995; Samaha et al., 1995). Dark nuclei only indicated the early stage of apoptosis which is accompanied by mirgination and condensation of chromatin.

All apoptosis data is entered into a computer file, providing spatial information relating apoptotic cells to position in colonic crypts. This method of data analysis allows the inventors to compare patterns of basal levels of apoptosis as a function of their spatial position in the crypt. This is important, as recent studies have been indicated that other colon cancer-related gene defects, such as mutations in the adnenomatous polyposis coli (APC) gene, cause unique spatial changes in apoptosis in the apparently normal colonic mucosa (Strater et al., 1995).

Gene mutations in neoplastic colon tissues.

The AOM-treated rat has been the main model used to identify agents for use as colon cancer chemopreventive agents in humans. Extensive knowledge about the molecular genetics of human colorectal cancer has been gathered over the past decade. In spite of the widespread use of this model, little is understood about the relevance of this model to human colon carcinogenesis, in terms of specific gene mutation. The inventors have assessed the effects of the NSAIDs sulindac sulfoxide and sulindac sulfone on Ki-ras mutations in the AOM-treated rat. These two NSAIDs are of interest in that the sulfoxide form of this NSAID inhibit cycloxygenase and prostaglandin synthesis, while the sulfone form does not. Both forms inhibit carcinogenesis in the AOM-treated rat, with similar potencies. Sulindac sulfone caused a reduction in the frequency of AOM-induced codon 12 mutations in Ki-ras, from 19/31 (61%) to 5/35 (14%).

There was some indication of dose-dependency to this effect, over the range of 0–1000 ppm sulindac sulfone administration in the food. These results were similar to those found by Singh et al. (1994), who reported that another NSAID, piroxicam, reduced Ki-ras mutation frequencies in this model.

REFERENCES

The following references, to the extent that they provide exemplary procedural or other details supplementary to those set forth herein, are specifically incorporated herein by reference.

U.S. Pat. No. 4,413,141
U.S. Pat. No. 4,330,559
U.S. Pat. No. 4,925,835
U.S. Pat. No. 4,499,072
U.S. Pat. No. 5,002,879
U.S. Pat. No. 4,859,452
U.S. Pat. No. 5,814,625
U.S. Pat. No. 5,843,929

Alberts, Hixson, Ahnen, Bogert, Einspahr, Paranak, Brendel, Gross, Pamukcu, Burt, "Do NSAIDs exert their colon cancer chemoprevention activities through the inhibition of mucosal prostaglandin synthetase?" *J. Cell. Biochem. Supp.*, (22):18–23, 1995.

Arber, Han, Sgambato, Piazza, Delohery, Begemann, Weghorst, Kim, Pamukcu, Ahnen, Reed, Weinstein, Holt, "A K-ras oncogene increases resistance to sulindac-induced apoptosis in rat enterocytes," *Gastroenterology*, (113):1892–1990, 1997.

Ausubel, ed., "Current protocols in molecular biology," New York: John Wiley & Sons, Auvinen, "Cell transformation, invasion, and angiogenesis: a regulatory role for ornithine decarboxylase and polyamines?," [editorial], *J. Natl. Cancer Inst.*,(89):533–7, 1997.

Bacus and Bacus, "A method of correcting DNA ploidy measurement in tissue sections," *Mod. Pathol.,* 7:652–666, 1994.

Bacus and Grace, "Optical microscope system for standardized cell measurement and analyses," *Appl. Optics.,* 26:3280–3293, 1987.

Bedi, Pasricha, Akhtar, Barber, Bedi, Giardiello, Zehnbaurer, Hamilton, Jones, "Inhibition of apoptosis during development of colorectal cancer," *Cancer Res.* (55):1811–1816, 1995.

Braverman, Standiewicz, Godlstein, Patz, Morali, Jacobsohn," Ornithine decarboxylase: an unreliable marker for the identification of population groups at risk for colonic neoplasia," *Am. J. Gastroenterology,* 85:723–726, 1990.

Boolbol, Dannenberg, Chadburn, Martucci, Guo, Ramonetti., Abreu-Goris, Newmark, Lipkin, deCosse, Bertagnolli, "Cyclooxygenase 2 overexpression and tumor formation are blocked by sulindac in a murine model of familial adenomatous polyposis," *Cancer Res.,* (56):2256–2560, 1996.

Boyle, Meyskens, Garweal, Gerner, "Polyamine contents in rectal and buccal mucosae in human treated with oral difluoromethylomithine," *Cancer Epi Biomarkers Prev.,* 1:131–135, 1992.

Bumer, Loeb, "Mutations in the KRAS2 oncogene during progressive stages of human colon carcinoma," *Proc. Natl. Acad. Sci. U.S.A.,* 86(7):2403–7, 1989.

Bussey, "Historical developments in familial adenomatous polyposis," In: Lemuel Herrera (ed), Familial Adenomatous Polyposis, pp. 1–22, Alan R. Liss, Inc. New York, 1990.

Carethers, "The cellular and molecular pathogenesis of colorectal cancer," *Gastroenterology Clinics of north America*, (25):737–754, 1996.

Croghan, Aicken, Meyskens, "Dose-related α-difluoromethylornithine ototoxicity," *Am. J. Clin. Oncol.*, (14):331–5, 1991.

Delage, Chastre, Empereur, Wicek, Veissiere, Capeau, Gespach, Cherqui, "Increased protein kinase C alpha expression in human colonic Caco-2 cells after insertion of Ha-ras or polyoma virus middle T oncogenes," *Cancer Res.,* (53):2762–70, 1993.

DiSario, Alberts, Tietz, Khullar, Bohrman, Larsen, Hixson, Samowitz, Reading, Buys, Dawson, Burt, "Sulindac induces regression and prevents progression of sporadic colorectal adenomas," *Gastroenterology (AGA Abstract)*, April 1997.

DuBois, Giardiello, Smalley, "Nonsteroidal anti-inflammatory drugs, eicosanoids, and colorectal cancer prevention," *Gastroenterology*, (25):773–791, 1996.

Erdman, Wu, Hixson, Ahnen, Gerner, "Assessment of Mutations in Ki-ras and P53 in colon cancers from azoxymethane-and dimethylhydrazine-treated rats," *Mol. Carcin.*, (19):137–144, 1997.

Gann, Manson, Glynn, Buring, Hennedens, "Low-dose aspirin and incidence of colorectal tumors in a randomized trial," *J. Natl. Cancer Inst.,* 85:1220–1224, 1993.

Gerner, Garewal, Emerson, Sampliner, "Gastrointestinal tissue polyamine contents of patients with Barrett's esophagus treated with a-difluoromethylomithine," *Cancer Epidemoil. Biomarkers Prev.,* 3:325–330, 1994.

Giardiello, Hamilton, Hylind, Yang, Tamez, Casero, "Ornithine decarboxylase and polyamines in familial adenomatous polyposis," *Cancer Res.*, (57):199–201, 1997.

Giovannucci, Rimm, Stampfer, Colditz, Ascherio, Willett, "Aspirin use and the risk for colorectal cancer and adenomas in male health professionals," *Ann. Intern. Med.,* 121:241–246, 1994.

Greenberg, Baron, Freeman, Mandel, Haile, "Reduced risk of large-bowel adenomas among aspirin users," *J. Natl. Cancer Inst.,* 85:912–916, 1993.

Hanif, Pittas, Feng, Koutsos, Qiao, Staino-Coico, Shiff, Rigas, "Effects of nonsteroidal anti-inflammatory drugs on proliferation and on induction of apoptosis in colon cancer cells by a prostaglandin-independent pathway," *Biochemical Pharmacology*, (52):237–245, 1996.

Hixson, Emerson, Shassetz, Gerner, "Sources of variability in measurements of ornithine decarboxylase activity and polyamine contents in colorectal mucosa," *Cancer Epidemoil. Biomarkers Prev.,* 3:317–323, 1994.

Hixson, Garewal, McGee, Sloan, Fennerty, Sampliner, Gerner, "Ornithine decarbolylase and polyamines in colorectal nelplasia and adjacent nucosa," *Cancer Epidemiology Biomarkers Prev.,* 2:369–374, 1993.

Jiang, Kahn, Guillem, Lu, Weinstein, "Rapid detection of ras oncogenes in human tumors, applications to colon, esophageal, and gastric cancer," *Oncogene,* 4:923–928, 1989.

Kerr, Winterford, Harmon, "Apoptosis: its significance in cancer and cancer therapy," *Cancer*, (73):2013–2026, 1994.

Kerr, Searle, Harmon, Bishop, "Apoptosis," In: *Perspectives on mammalian cell death*, Potten (ed), Oxford Press, NY, N.Y., 93–128, 1987.

Kerr, Wyllie, Currie, "Apoptosis: a basic biological phenomenon with wide-ranging implications in tissue kinetics," *Br. J. Cancer,* 26:239–257, 1972.

Keshgegian, Cnaan, "Proliferation markers in breast carcinoma. Mitotic figure counting, S-phase fraction, PCNA, Ki-67 and MIB-1," *Am. J Clin. Pathol.,* 104:1042–1049, 1995.

Kingsnorth, King, Diekema, McCann, Ross, Malt, "Inhibition of ornithine decarboxylase with 2-difluoromethylornithine: reduced incidence of dimethylhydrazine-induced colon tumors in mice," *Cancer Res.*, (43):2545–2549, 1983.

Kubota, Kiyosawa, Nomura, Yamada, Seyama, "Ornithine decarboxylase overexpression in mouse 10T1/2 fibroblasts: cellular transformation and invasion," *J. Natl. Cancer Inst.*,(89):567–71, 1997.

Kulkarni, Zang, Kelloff, Reddy, "Effect of the chemopreventive agents piroxicam and D,L-□-difluoromethylornithine on intermediate biomarkers of colon carcinogenesis," *Carcinogenesis*, (13):995–1000, 1992.

Ladenheim, Garcia, Titzer, Herzenbert, Lavori, Edson, Omary, "Effect of Sulindac on sporadic colonic polyps," *Gastroenterology*, 108:1083–1087, 1995.

Laemmli, "Cleavage of structural proteins during the assembly of the head of bacteriophageT4," *Nature*, 227(259): 680–5, 1970.

Lanza, Walker, Bortnichak, Dreyer, "Peptic ulcer and gastrointestinal hemorrhage associated with nonsteroidal anti-inflammatory drug use in patients younger than 65 years. A large health maintenance organization cohort study." *Arch. Intern. Med*, 155:1371–1377, 1995.

Levin, Chamberlain, Prados, Choucair, Berger, Silver, et al., "Phase I-II study of eflornithine and mitogauzone combined in the treatment of recurrent primary brain tumors," *Cancer Treat. Rep.*, (71):459–64, 1987.

Liao, Brewer, Zavada, Pastorek, Pasterekova, Manetta, Berman, DiSaia, Stanbridge, "Identification of the MN antigen as a diagnostic biomarker of cervical intraepithelial squamous and glandular neoplasi and cervical carcinomas," *Am. J. Pathol.*, 145:598–609, 1994.

Lipkin, "New rodent models for studies of chemopreventive agents," *J. Cell Biochem Suppl*(28–29):144–7, 1997.

Losi, Roncucci, di Gregorio, de Leon, Benhattar, "K-ras and p53 mutations in human colorectal aberrant crypt foci," *Journal of Pathology*, 178(3):259–63, 1996

Lowy, Willumsen, "Function and regulation of ras,"*Annu Rev Biochem* (62):851–91, 1993.

Luk, Baylin, "Onithine decarboxylase as a biological marker in familial colonic polyposis," *N. Eng. J Med.*, (311): 80–83, 1984.

Lupulescu, "Prostaglandins, their inhibitors and cancer," *Prostaglandins, Leukotrienes, and Essential Fatty Acids*," (54):83–94, 1996.

Matter A: Microcinematographic and electron microscopic analysis of target cell lysis induced by cytotoxic T lumphocytes," *Immunology*, 36:179–190, 1979.

McCann, Pegg, "Ornithine decarboxylase as an enzyme target for therapy," *Pharmacol. Ther.*, (54):195–215, 1992.

Meyskens, Kingsley, Glatrke, Loescher, Booth, "A phase II study of α-difluoromethylornithine (DFMO) for the treatment of metastatic melanoma," *Invest. New Drugs*, (4):257–62, 1986.

Meyskens, Emerson, Pelot, Meshkinpour et al., "Dose de-escalation chemoprevention trial of α-difluoromethylomithine in patients with colon polyps," *J. Natl. Cancer Inst.*, 86(15):1122–1130, 1994.

Meyskens, Gerner, "Development of difluoromethylomithine as a chemoprevention agent for the management of colon cancer," *J. Cell. Biochem.*, 22:126–131, 1995.

Meyskens, Pelot, Meshkinpour, Plezia, Gerner, Emerson, "Preliminary results of a phase Iia of difluoromethylornithine (DFMO) to prevent colon cancer," In: *Cancer Chemoprevention*, Kelloff (ed), CRC Press, Inc., Boca Raton, Fla., 36:541–555, 1992.

Moorghen, Inc, Finney, Sunter, Appleton, Watson, "A protective effect of Sulindac against chemically-induced primary colonic tumors in mice," *J. Pathol.*, 156:341347, 1988.

Muscat, Stellman, Wynder, "Nonsteroidal antiinflammatory drugs and colorectal cancer," *Cancer*, 74:1847–1854, 1994.

Narisawa, Sato, Tani, Kudo, Takahashi, Goto, "Inhibition of development of methylnitrosourea-induced rat colon tumors by indomethacin treatment," *Cancer Research* 41(5):1954–7, 1981.

Nigro, Bull, Boyd, "Importance of the duration of inhibition on intestinal carcinogenesis by difluoromethylornithine in rats," *Cancer Lett.*,(35):183–8, 1987.

Nowels, Homma, Seidenfeld, Oyasu, "Prevention of the inhibitory effects of alphadiflouromethylornithine on rat urinary bladder carcinogenesis by exogenous putrescine", *Cancer. Biochem. Biophys.*,(8):257–63, 1986.

Pasricha, Bedi, O'Connor, Rashid, Akhtar, Zahurak, Piantadose, Hamilton, Giardiello, "The effects of sulindac on colorectal proliferation and apoptosis in familial adenomatous polyposis," *Gastroenterology*, 109:994–998, 1995.

Payne, Bjore, Schultz, "Change in the frequency of apoptosis after low- and high-dose x-iradiation of human lymphocytes," *J. Leuk. Biol.*, 52:433–440, 1992.

Payne, Bernstein, Bernstein, "Apoptosis overview emphasizing the role of oxidative stress. DNA damage and signal transduction pathways," *Leukemia Lumphoma*, 19:43–93, 1995.

Pegg, "Recent advances in the biochemistry of polyamines in eukaryotes," *Biochem. J.*, (234):249–262, 1986.

Pegg, "Polyamine metabolism and its importance in neoplastic growth and a target for chemotherapy," *Cancer Res.*, (48):759–74, 1988.

Piazza, Alberts, Hixson, Paranka, Li, Finn, Bogert, Guillen, Brendel, Gross, Speri, Ritchie, Burt, Ellsworth, Ahnen, Pamukcu, "Sulindac sulfone inhibits azoxymethane-induced colon carcinogenesis in rats without reducing prostaglandin levels," *Cancer Res.*, (57):2909–2915, 1997a.

Piazza, Rahm, Krutzsch, Speri, Paranka, Gross, Brendel, Burt, Alberts, Pamukcu, Ahnen, "Antineoplastic drugs sulindac sulfide and sulfone inhibit cell growth by inducing apoptosis," *Cancer Res.*, (55):311 3116, 1995.

Piazza, Rahm, Finn, Fryer, Li, Stumen, Pamakcu, Ahnen, "Apoptosis primarily accounts for the growth-inhibitory properties of sulindac metabolites and involves a mechanism that is independent of cyclooxygenase inhibition, cell cycle arrest, and p53 induction," *Cancer Res.*, (57): 2452–2459, 1997b.

Pollard, Luckert, "Prevention and treatment of primary intestinal tumors in rats by piroxicam," *Cancer Res.*, 49:6471–6473, 1989.

Porter, Herrera-Omelas, Pera, Petrelli, Mittleman, "Polyamine biosynthetic activity in normal and neoplastic human colorectal tissue," *Cancer*, 60:1275–1281, 1987.

Rao, Rivenson, Simi, Zang, Kelloff, Steele, Reddy, "Chemoprevention of colon carcinogenesis by sulindac, a nonsteroidal anti-inflammatory agent," *Cancer Res.*, (55):1464 1472, 1995.

Reddy, Maruyama, Kelloff, "Dose-related inhibition of colon carcinogenesis by dietary prioxicam, a nonsteroidal anti-inflammatory drug, during different stages of rat colon tumor development," *Cancer Res.*, 47:5340–5346, 1987.

Reddy, Sugie, "Effect of different levels of omega-3 and omega-6 fatty acids on azoxymethane-induced colon carcinogenesis in F344 rats," Cancer Res., (48):6642–647, 1988.

Reddy, Nayini, Tokumo, Rigotty, Zang, Kelloff, "Chemoprevention of colon carcinogenesis by concurrent administration of piroxicam, a nonsteroidal anti-inflammatory drug with D,L-α-difluoromethylomithine, and ornithine decarboyxlase inhibitor, in diet," Cancer Res., (50):2562–2568, 1990.

Rousset, "The human colon carcinoma cell lines HT-29 and Caco-2: two in vitro models for the study of intestinal differentiation," Biochimie, (68):1035–1040, 1986.

Russell, Rosenau, Lee, "Cytolysis induced by human lumphotoxin. Cinemicrographic and electron microscopic observations," Amer. J. Pathol., 69:103–118, 1972.

Samaha, Asher, Payne, Garewal, Sampliner, Berstein, "Evaluation of cell ceath in EBV-transformed lymphocytes using agarose gel electrophoresis, light microscopy and electron microscopy. I. Induction of classic apoptosis by the bile salt, sodium deoxycholate," Leukemia Lymphoma, 19:95–105, 1995.

Samaha, Bernstein, Payne, Garewal, Sampliner, Berstein, "Bile salts induce apoptosis in goblet cells of the normal human colonic ucosa: relevance to colon cancer patients," Acta Microscopica, 4:43–58, 1995. Samaha, Kelloff, Steele, Rao, Reddy, "Modulation of apopotsosi by sulindac, curcumin, phenylethyl-3-methylcaffeate, and 6-phenylhexyl isothiocyanate, apoptotic index as a biomarker in colon cancer chemoprevention and promotion," Cancer Res., (57):1301–1305, 1997.

Sanderson, "The mechanism of lymphocyte-mediated cytotoxicity," Biol. Rev., 56:153197,1981.

Searle, Kerr, Bishop, "Necrosis and apoptosis: distinct modes of cell death with fundamentally different significance," Pathol. Annual., 17:229–259, 1982.

Shiff, Koutsos, Qiao, Rigas, "Nonsteroidal antiinflammatory drugs inhibit the proliferation of colon adenocarcinoma cells: effects on cell cycle and apoptosis," Esp. Cell. Res., 222:179–188, 1996.

Shiff, Qiao, Tsai, Rigas, "Sulindac sulfide, an aspirin-like compound, inhibits proliferation, causes cell cycle quiescence, and induces apoptosis in HT-29 colon adenocarcinoma cells," J. Clin. Invest., 96:491–503, 1995.

Shirasawa, Furuse, Yokoyama, Sasazuki, "Altered growth of human colon cancer cell lines disrupted at activated Ki-ras," Science (260):65–88, 1993.

Singh and Reddy, "Molecular markers in chemoprevention of colon cancer. Inhibition of expression of ras-p21 and p53 by sulindac during azoxymethane-induced colon carcinogenesis," Annals of the New York Academy of Sciences, (768):205–209, 1995.

Singh, Kelloft Reddy, "Intermediate biomarkers of colon cancer, modulation of expression of reas oncogene by chemopreventive agents during azoxymethane induced colon carcinogenesis," Carcinogenesis, (14):669–704, 1993.

Singh, Kulkami, Kelloff, Reddy, "Modulation of azoxymethane-induced mutational activation of ras protooncogenes by chemopreventive agents in colon carcinogenesis," Carcinogenesis, (15):1317–1323, 1994.

Su, Kinzler, Vogelstein, Preisinger, Moser, Luongo, Gould, Dove, "Multiple intestinal neoplasia caused by a mutation in the murine homolog of the APC gene," Science, (256):668–670, 1992.

Strater, Koretx, Gunthert, Moller, "In situ detection of enterocytic apoptosis in normal colonic mucosa and in familial adenomatous polyposis," Gut, 37:819–825, 1995.

Tempero, Nishioka, Knott, Zetterman, "Chemoprevention of mouse colon tumors with difluromethylomithine during and after carcinogen treatment," Cancer Res., (49):5793–5797, 1989.

Thompson, Meeker, Herbst, Ronan, Minocha, "Effect of concentration of D,L-2-difluoromethylomithine on murine mammary carcinogenesis," Cancer Res, (45):1170–3, 1985.

Thompson, Briggs, Paranka, Piazza, Brendel, Gross, Speri, Parnucku, Ahnen, "Inhibition of mammary carcinogenesis by sulfone metabolite of sulindac," J. Natl. Cancer Inst., (87):125–1260, 1995.

Trainer, Kline, McCabe, Faucette, Field, Chaikin, Anzano, Rieman, Hoffstien, Li, Gennaro, Buscarino, Lynch, Poste, Grieg, "Biological characterization and oncogene expression in human colorectal carcinoma cell lines," Int. J. Cancer, (41):287–296, 1988.

Vane, and Botting, "Mechanism of action of aspirin-like drugs," Sem. in Arthritis and Rheumatism, (26):2–10, 1997.

Vivona, Shpitz, Medline, Bruce, Hay, Ward, Stem, Gallinger, "K-ras mutations in aberrant crypt foci, adenomas and adenocarcinomas during azoxymethane-induced colon carcinogenesis," Carcinogenesis14(9):1777–81, 1993.

Vogelstein, Fearon, Hamilton, "Genetic alterations during colorectal tumor development," N. Engl. J Med., (319):525–532, 1988.

Voytesek, Bartek, Midglely, Lane, "An immunochemical analysis of the human nuclear phosphoprotein -53. New monoclonal antibodies and epitope mapping using recombinant p53," J. Immunol. Methods, 151:237–244, 1992.

Walker, Harmon, Glove, Kerr, "Patterns of cell death," Meth. Archiev. Exp. Pathol., 13:18–54, 1988.

Ward, Todd, Santiago, O'Connor, Hawkins, "Activation of the K-ras oncogene in colorectal neoplasms is associated with decreased apoptosis," Cancer, (79): 110–1113,1997.

Weeks, Herrmann, Nelson, Slaga, "a-Diflouromethylornithine, an irreversible inhibitor of ornithine decarboxylase, inhibits tumor promoter-induced polyamine accumulation and carcinogenesis in mouse skin," Proc. Natl. Acad. Sci. U.S.A., (79):6028–32, 1982.

Wyllie, "Cell death: a new classification separation apoptosis from necrosis," In: cell death in biology and pathology, Bowen and Lockshin (eds), Chapman and Hall, NY, N.Y., 9–34, 1981.

Xu, Real, Welt, Schussler, Oettgen, Oettgen, Old, "Expression of TAG-72 in normal colon, transistional mucosa and colon cancer," Int. J. Cancer, 44:985–989, 1989.

Yang, Shamsuddin, "A new murine monoclonal antibody, CMU10, as a marker for colonic carcinoma and precancerous conditions," Arch. Pathol. Lab. Med., 119:454–457, 1995.

What is claimed is:

1. A method for preventing and/or treating cancer in a patient having an Ki-ras-dependent cancer sensitive to the combination below comprising administering an effective amount of difluoromethylornithine (DFMO) in combination with an enhanced effective amount of the non-steroidal anti-inflammatory drug, sulindac, to said patient.

2. The method of claim 1, wherein sulindac is administered at a dose of about 10 to 1500 mg/day.

3. The method of claim 1, wherein sulindac is administered at a dose of about 10 to 400 mg/day.

4. The method of claim 1, wherein DFMO is administered at a dose of about 0.05 to about 5.0 gm/M$^2$/day.

5. The method of claim 1, wherein DFMO is administered at a dose of about 0.05 to about 0.50 gm/M$^2$/day.

6. The method of claim 1, wherein the cancer is colon cancer, breast cancer, pancreatic cancer, brain cancer, lung cancer, stomach cancer, a blood cancer, skin cancer, testicular cancer, prostate cancer, ovarian cancer, liver cancer, esophageal cancer.

7. The method of claim 6, wherein the cancer is colon cancer.

8. The method of claim 7, wherein the colon cancer is familial adenomatous polyposis.

9. The method of claim 1, wherein DFMO is administered prior to sulindac.

10. The method of claim 1, wherein DFMO is administered after sulindac.

11. The method of claim 1, wherein DFMO is administered at the same time as sulindac.

12. The method of claim 1, wherein DFMO is administered at least a second time.

13. The method of claim 1, wherein sulindac is administered at least a second time.

14. The method of claim 1, wherein said patient has a solid tumor, and said method further comprises resection of said solid tumor.

15. The method of claim 14, wherein DFMO and sulindac are admininstered prior to said resection.

16. The method of claim 14, wherein DFMO and sulindac are admininstered after said resection.

17. The method of claim 1, wherein said patient has a solid tumor, and DFMO and sulindac are administered directly to said solid tumor.

18. The method of claim 1, wherein DFMO and sulindac are administered systemically.

19. The method of claim 1, wherein said patient has a solid tumor, and DFMO and sulindac are administered into the regional vasculature of said solid tumor.

20. The method of claim 1, wherein said patient has a solid tumor, and DFMO and sulindac are administered into the region lymph system of said solid tumor.

21. The method of claim 1, wherein DFMO and sulindac are administered by different routes.

* * * * *

UNITED STATES PATENT AND TRADEMARK OFFICE
CERTIFICATE OF CORRECTION

PATENT NO. : 6,258,845 B1
DATED : July 10, 2001
INVENTOR(S) : Eugene W. Gerner and Frank L. Meyskens, Jr.

It is certified that error appears in the above-identified patent and that said Letters Patent is hereby corrected as shown below:

<u>Title page,</u>
Item [73], line 3, please delete "Arizonia" and insert -- Arizona -- therefor; and please insert -- on -- before "Behalf of".
Line 4, please delete "Arizonia" and insert -- Arizona -- therefor.

Signed and Sealed this

Seventh Day of May, 2002

Attest:

JAMES E. ROGAN
Attesting Officer    Director of the United States Patent and Trademark Office